United States Patent [19]

Lafferty et al.

[11] Patent Number: 4,959,360
[45] Date of Patent: Sep. 25, 1990

[54] α-ADRENERGIC RECEPTOR ANTAGONISTS

[75] Inventors: John J. Lafferty, Levittown; Robert M. Demarinis, Ardmore; Joseph W. Venslavsky, Wayne, all of Pa.

[73] Assignee: SmithKline Beecham Corporation, Philadelphia, Pa.

[21] Appl. No.: 361,874

[22] Filed: Jun. 6, 1989

Related U.S. Application Data

[63] Continuation-in-part of Ser. No. 200,884, Jun. 1, 1988, abandoned.

[51] Int. Cl.$^5$ .................. C07D 513/06; A61K 31/38
[52] U.S. Cl. .................................. 514/217; 540/581; 540/79; 514/81
[58] Field of Search ................ 540/581, 79; 514/217, 514/81

[56] References Cited

U.S. PATENT DOCUMENTS

| | | | |
|---|---|---|---|
| 3,649,644 | 3/1972 | Sonntag et al. | 540/581 |
| 3,833,591 | 9/1974 | McManus | 260/239 R |
| 3,856,910 | 12/1974 | Nedelec et al. | 514/215 |
| 3,904,645 | 9/1975 | McManus | 260/326.5 B |
| 3,906,000 | 9/1975 | McManus | 260/326.5 B |
| 4,469,634 | 9/1984 | DeMarinis | 260/239 BB |
| 4,769,368 | 9/1988 | Kaiser et al. | 514/217 |
| 4,833,244 | 5/1989 | Kosley et al. | 540/581 |

FOREIGN PATENT DOCUMENTS

| | | | |
|---|---|---|---|
| 2194786 | 3/1988 | European Pat. Off. | 540/581 |
| 0144286 | 9/1982 | Japan | 514/217 |
| 8700522 | 1/1987 | PCT Int'l Appl. | |

Primary Examiner—David B. Springer
Attorney, Agent, or Firm—Mary E. McCarthy; Stuart R. Suter; Edward T. Lentz

[57] ABSTRACT

α-adrenoceptor antagonists having the formula:

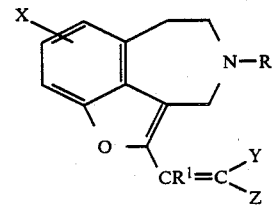

which are useful to produce α-adrenoceptor antagonism, pharmaceutical compositions including these antagonists, and methods of using these antagonist to produce α-adrenoceptor antagonism in mammals.

16 Claims, No Drawings

α-ADRENERGIC RECEPTOR ANTAGONISTS

This application is a continuation-in-part of U.S. Ser. No. 07/200,884, filed on June 1, 1988, abandoned.

FIELD OF THE INVENTION

This invention relates to novel substituted 2-ethenyl-3,4,5,6 tetrahydrofuro[4,3,2-ef][3]benzazepine compounds that are α-adrenergic receptor antagonists.

BACKGROUND OF THE INVENTION

The autonomic nervous system is separated into the cholinergic and adrenergic nervous systems. Norepinephrine, the neurotransmitter of the adrenergic nervous system, exerts its activity by interaction with receptors (adrenoceptors) on the effector organs or on the nerve endings. The adrenoceptors are of two primary types: α and β. Based upon selectivity of the receptors for a series of aqonists and antagonists, the α adrenoceptors have been subdivided into $\alpha_1$ and $\alpha_2$ subtypes.

A large amount of experimental evidence now supports the view that the $\alpha_2$ subtype is a heterogeneous adrenoceptor class. (For a general review see Timmermans and Van Zwieten, *J. Med. Chem.*, 25, 1389 (1982)). Experiments using 6 chloro 9 (3-methyl-2-butenyloxy)-3-methyl 2,3,4,5-tetrahydro IH-3-benzazepine (SK&F 104078) demonstrated that the classical adrenoceptors are heterogeneous and can be divided into SK&F 104078 — insensitive and SK&F 104078— sensitive $\alpha_2$ adrenoceptors. The latter variously are referred to as postjunctional $\alpha_2$ adrenoceptors or, preferably, $\alpha_3$ adrenoceptors, U.S. Pat. No. 4,683,229, July 28, 1987.

As one of the primary regulators of peripheral vascular tone, α adrenoceptors long have been the targets of efforts to develop agents effective in changing vascular tone for use in treating diseases, such as hypertension, in which alterations in vascular resistance produce therapeutic benefits. Antihypertensive compounds presently in clinical use that function via interaction with α adrenoceptors include methyldopa, clonidine, and prazosin. Efforts to modulate sympathetic tone through interactions with α adrenoceptors have resulted in several compounds that interact somewhat selectively with $\alpha_1$ or $\alpha_2$ adrenoreceptors. Selective agonists include phenylephrine and methoxamine which preferentially activate $\alpha_1$ receptors; and clonidine, α-methyl-norepinephrine, and tramazoline which preferentially activate $\alpha_2$ adrenoceptors. Examples of selective α-adrenoceptor antagonists include prazosin which has high selectivity for $\alpha_1$ adrenoceptors; and the $\alpha_2$-selective blockers yohimbine and rauwolscine.

U.S. Pat. No. 4,469,634, dated Sept. 4, 1984, describes allyloxy- and allythio2,3,4,5-tetrahydro-lH 3-benzazepines useful as intermediates for preparing $\alpha_2$ adrenoceptor affinity resins and as antihypertensive agents.

U.S. Pat. Nos. 3,833,591, 3,904,645, and 3,906,000 disclose substituted compounds of the following base structure:

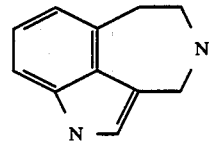

These compounds are useful as hypoglycemic agents.

PCT Application Number WO 87/00522 describes a series of 4-aminotetrahydrobenz[c,d]indoles and tetrahydroazepino[3,4,5-c,d]indoles having the general formula:

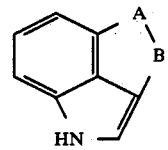

in which A—B is —$CH_2$—CH(NRR)—$CH_2$ or —$CH_2$—$CH_2$—NR—$CH_2$. These compounds are dopamine agonists useful as hypotensives.

SUMMARY OF THE INVENTION

The present invention resides in the discovery that various substituted-2-ethenyl 3,4,5,6-tetrahydrofuro[4,3,2-ef][3]benzazepine compounds are α-adrenoceptor antagonists. Presently preferred compounds of the invention include:

7-chloro-2-ethylenyl-3,4,5,6-tetrahydrol-4-methylfuro[4,3,2-ef][3]benzazepine;

7-chloro-3,4,5,6-tetrahydro-4-methyl-2-(2-methyl-1-propenyl)furo[4,3,2-ef][3]benzazepine;

ethyl (E)-3-(7chloro-3,4,5,6-tetrahydro-4-methylfuro[4,3,2-ef][3]benzazepin-2-yl)-2propenoate;

ethyl (E)-3-(7-chloro-3,4,5,6-1 -tetrahydrofuro[4,3,2-ef][3]benzazepin-2-propenoate;

ethyl (E)-3-(7-chloro-3,4,5,6-tetrahydro-4-(2-propenyl)furo[4,3,2-ef][3]benzazepin-2-yl]-2-propenoate;

ethyl (E)-3-(7-chloro-3,4,5,6- tetrahydro-4methylfuro[4,3,2-ef][3]benzazepin-2-yl)-2-methyl-2-propenoate;

ethyl (E)-3(7-chloro-3,4,5,6-tetrahydro-4-methylfuro[4,3,2-ef][3]benzazepin-2-yl)-2-propyl-2-propenoate;

ethyl (Z)-3 (7 chloro 3,4,5,6-tetrahydro 4-methylfuro[4,3,2-ef][3]benzazepin 2-yl) 2-fluoro-2-propenoate;

ethyl- (E) 2-chloro-3-(7-chloro-3,4,5,6-tetrahydro-4-methylfuro[4,3,2 ef][3]benzazepin-2yl)-2-propenoate;

ethyl (Z)-2-chloro-3-(7 chloro-3,4,5,6 tetrahydro-4-methylfuro[4,3,2 ef][3]benzazepin-2-yl)-2-propenoate;

ethyl (Z)-2-bromo-3-(7-chloro 3,4,5,6 tetrahydro-4-methylfuro[4,3,2-ef][3]benzazepin-2-yl)-2-propenoate;

(E)-3-(7-chloro-3,4,5,6 tetrahydro 4-methylfuro-[4,3,2-ef][3]benzazepin-2-yl) 2-propenoic acid;

methyl (E) 3 (7 chloro 3,4,5,6 tetrahydro-4-methylfuro[4,3,2 ef][3]benzazepin 2-yl)-2-propenoate;

(E)-3-(7-chloro 3,4,5,6 tetrahydro 4-methylfuro-[4,3,2 ef][3]benzazepin 2-yl)-2-propenamide;

(E)-3-(7-chloro-3,4,5,6tetrahydro 4-methylfuro-[4,3,2-ef][3]benzazepin-2-yl)-N-methyl-2-propenamide;

(E)-3-(7-chloro 3,4,5,6tetrahydro 4methylfuro-[4,3,2-][3]benzazepin-2-yl)-N,N-dimethyl-2-propenamide;

(E)-3-(7-chloro-3,4,5,6-tetrahydro-4-methylfuro-[4,3,2-ef][3]benzazepin-2-yl)-N,2-dimethyl-2-propenamide;

(E)-3-(7chloro 3,4,5,6-tetrahydro 4-methylfuro-[4,3,2-ef][3]benzazepin-2-yl) 2propenenitrile;

(E)-4-(7-chloro 3,4,5,6tetrahydro 4-methylfuro-[4,3,2-ef][3]benzazepin-2-yl)-3-buten-2-one;

(E)-7chloro-3,4,5,6tetrahydro 4-methyl-2-[2-(methylsulfonyl)ethenyl]furo[4,3,2-ef][3]benzazepine;

(E)-2-(7-chloro 3,4,5,6tetrahydro-4-methylfuro-[4,3,2-ef][3]benzazepin 2-yl)-N,N dimethylethenesulfonamide;

diethyl (E)-[2(7chloro 3,4,5,6-tetrahydro-4-methyl-furo[4,3,2ef][3]benzazepin 2-yl)ethenyl]phosphonate;

methyl (Z) 3-(7-chloro 3,4,5,6-tetrahydro-4-methyl-furo[4,3,2-ef][3]benzazepin-2-yl)-2-propenoate;

ethyl (E)-3-(7-chloro 4-ethyl 3,4,5,6-tetrahydrofuro[4,3,2-ef][3]benzazepin-2-yl)-2-propenoate;

(E)-3(7-chloro 3,4,5,6-tetrahydro-4-methylfuro-[4,3,2-ef][3]benzazepin-2-yl)-2-propen-1-ol;

(7-chloro-3,4,5,6-tetrahydro-4-methyl 2-[2-[(phenylmethoxy)methyl]ethenyl]furo[4,3,2-ef][3benzazepine;

(E) 1(7-chloro-3,4,5,6-tetrahydro-4-methylfuro-[4,3,2-ef][3]benzazepin 2-yl)-1-hexen-3-one;

(E)-1-(7-chloro-3,4,5,6tetrahydro-4-methylfuro-[4,3,2-ef][3]benzazepin-2-yl)-1-hepten-3-one;

(E)-1-(7-chloro-3,4,5,6-tetrahydro-4-methylfuro-[4,3,2-ef][3]benzazepin-2-yl)5-phenyl-1-pentene-3one;

(E)-3-(7-chloro-3,4,5,6-tetrahydro-4-methylfuro-[4,3,2-ef][3benzazepin-2-yl)-N-methyl-2-(2-hydroxyethyl)-2-propenamide;

(E)-3-(7-chloro-3,4,5,6-tetrahydro-4-methylfuro-[4,3,2-ef][3]benzazepin-2-yl)-N-ethyl-2-propenamide;

(E)-3-(7-chloro-3,4,5,6-tetrahydro-4-methylfuro-[4,3,2-ef][3]benzazepin-2-yl)-N,N-diethyl-2-propenamide;

(E)-3-(7-chloro-3,4,5,6-1 -tetrahydro-4-methylfuro-[4,3,2-ef][3]benzazepin-2-yl)-N-methyl-N-(phenylmethyl)-2-propenamide;

(E)-3-(7-chloro-3,4,5,6-tetrahydro-4-methylfuro-[4,3,2-ef][3]benzazepin-2yl)-N,N-bis(phenylmethyl)-2-propenamide;

propyl (E)-3-(7-chloro-3,4,5,6-tetrahydro-4-methyl-furo[4,3,2-ef][3]benzazepin-2-yl)-2-propenoate;

2-propyl (E)-3-(7-chloro-3,4,5,6-tetrahydro-4-methylfuro[4,3,2-ef][3]benzazepin-2-yl)-2-propenoate;

phenylmethyl (E)-3-(7-chloro-3,4,5,6-tetrahydro-4-methylfuro[4,3,2-ef][3]benzazepin-2-yl)-2-propenoate;

ethyl (E)-3(7chloro-3,4,5,6-tetrahydro-4-methylfuro[4,3,2-ef][3]benzazepin-2-yl)-2-phenyl-2-propenoate;

ethyl (Z)-3-(7-chloro-3,4,5,6-1 -tetrahydro-4-methylfuro[4,3,2-ef][3]benzazepin-2-yl)-2-phenyl-2-propenoate;

(E)-7-chloro-3,4,5,6-tetrahydro-4-methyl-2-[2-[1,1-dimethylethyl)sulfonyl]ethenyl]furo[4,3,2-ef][3]-benzazepine;

(E)-7-chloro-3,4,5,6-tetrahydro-4-methyl-2-[2-phenylsulfonyl)ethenyl]furo[4,3,2-ef][3]benzazepine;

(E)-2-(7-chloro-3,4,5,6-tetrahydro-4-methylfuro-[4,3,2-ef][3]benzazepin-2-yl)-N,N-diethyl-ethenesulfonamide;

(E)-2-(7-chloro-3,4,5,6-tetrahydro-4-methylfuro-[4,3,2-ef][3]benzazepin-2-yl)-N,N-dipropyl-ethenesulfonamide;

(E)-2-(7-chloro-3,4,5,6-tetrahydro-4-methylfuro-[4,3,2-ef][3]benzazepin-2-yl)-N-methyl-N-phenyl-ethenesulfonamide;

(E)-2-7-chloro-3,4,5,6-tetrahydro-4-methylfuro-[4,3,2-ef][3]benzazepin-2-yl)-N-methyl-N-phenylmethyl)-ethenesulfonamide; and (E)-2-(7-chloro-3,4,5,6-tetrahydro-4-methylfuro-[4,3,2-ef][3]benzazepin-2-yl)-N,N-bis(phenylmethyl)-ethene-sulfonamide;

or a pharmaceutically acceptable salt thereof.

In a further aspect of the invention there are provided methods of antagonizing α adrenoceptors in mammals, including humans, that comprise administering internally to a subject in need of such antagonism an effective amount of a substituted-2-ethenyl-3,4,5,6-tetrahydrofuro[4,3,2-ef][3]benzazepine compound.

Included in the present invention are pharmaceutical compositions that include compounds useful in the method of the invention and a suitable pharmaceutical carrier. Preferably, these compositions are used to produce α adrenoceptor antagonism and contain an effective amount of compounds useful in the methods of the invention.

DETAILED DESCRIPTION OF THE INVENTION

The presently invented compounds that are α-adrenoceptor antagonists are represented by the following Formula (I):

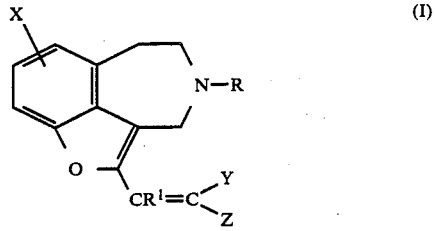

in which:

$X$ is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, $SC_{1-4}$alkyl, $S(CH_2)_{0-6}$aryl, $SCF_3$, or any accessible combination thereof of up to three substituents;

$R$ is H, $C_{1-6}$alkyl, or $C_{3-5}$alkenyl;

$R^1$ is H or $C_{1-6}$alkyl;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl;

$R^{12}$ is H, $C_{1-6}$alkyl, $COR^{14}$, or $SO_2R^{15}$;

$R^{13}$ is H or $C_{1-6}$alkyl;

$R^{14}$ and $R^{15}$ independently are $C_{1-6}$alkyl or $(CH_2)_{0-6}$aryl;

Y and Z independently are H, $NO_2$, $C_{1-6}$alkyl, $CH_2CH_2OH$, CN, $CH_2OR^2$, $CH_2SR^2$, $COR^2$, $CO_2R^2$, $CONR^3R^4$, $SO_2NR^3R^4$, $SO_3R^2$, $SO_2R^5$, $SOR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, halo, $CF_3$, or $(CH_2)_{0-6}$aryl;

$R^2$, $R^3$, and $R^4$ independently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$alkenyl, or $(CH_2)_{0-6}$aryl; or a pharmaceutically acceptable salt thereof.

As used herein $C_{1-6}$alkyl means straight or branched alkyl of one to six carbon atoms, $C_{3-5}$alkenyl means a straight or branched chain alkenyl having from 3 to 5 carbon atoms, aryl means a phenyl group which is unsubstituted or is substituted once or twice by $C_{1-6}$alkyl, $C_{1-6}$alkoxy, halo, $CF_3$ or CN, and "any accessible combination thereof" means any combination of up to three substituents on the phenyl moiety that is available by chemical synthesis and is stable.

Formula (Ia) includes presently preferred Formula (I) compounds:

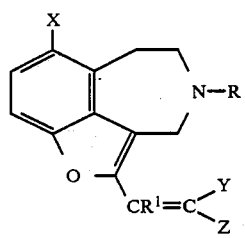

(Ia)

in which:

X is H, Cl, Br, F, I, $CF_3$, C1-6alkyl, $COR^{10}$, $CO_2R^{10}$, $CONR^{16}R^{11}$, CN, $NO_2$, $NR^{12}R^{13}$, $OR^{12}$, $SC_{1-04}$alkyl, $S(CH_2)_{0-6}$aryl, or $SCF_3$;

R is H, $C_{1-6}$alkyl, or $C_{3-5}$alkenyl;

$R^1$ is H or $C_{1-6}$alkyl;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl;

$R^{12}$ is H, $C_{1-6}$alkyl, $COR^{14}$, or $SO_2R^{15}$;

$R^{13}$ is H or $C_{1-6}$alkyl;

$R^{14}$ and $R^{15}$ independently are $C_{1-6}$alkyl or $(CH_2)_{0-6}$aryl; Y and Z independently are H, $NO_2$, $C_{1-6}$alkyl, $CH_2CH_2OH$, CN, $CH_2OR^2$, $CH_2SR^2$, $COR^2$, $CO_2R^2$, $CONR^3R^4$, $SO_2NR^3R^4$, $SO_3R^2$, $SO_2R^5$, $SOR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, halo, $CF_3$, or $(CH_2)_{0-6}$aryl;

$R^2$, $R^3$, and $R^4$ independently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$alkenyl, or $(CH_2)_{0-6}$aryl; or a pharmaceutically acceptable salt thereof.

Compounds of formula (I) are prepared by the synthetic pathways shown in Schemes I through III. In Schemes I through III, $R^3$, $R^4$, X, Y, and Z are as defined in Formula (I).

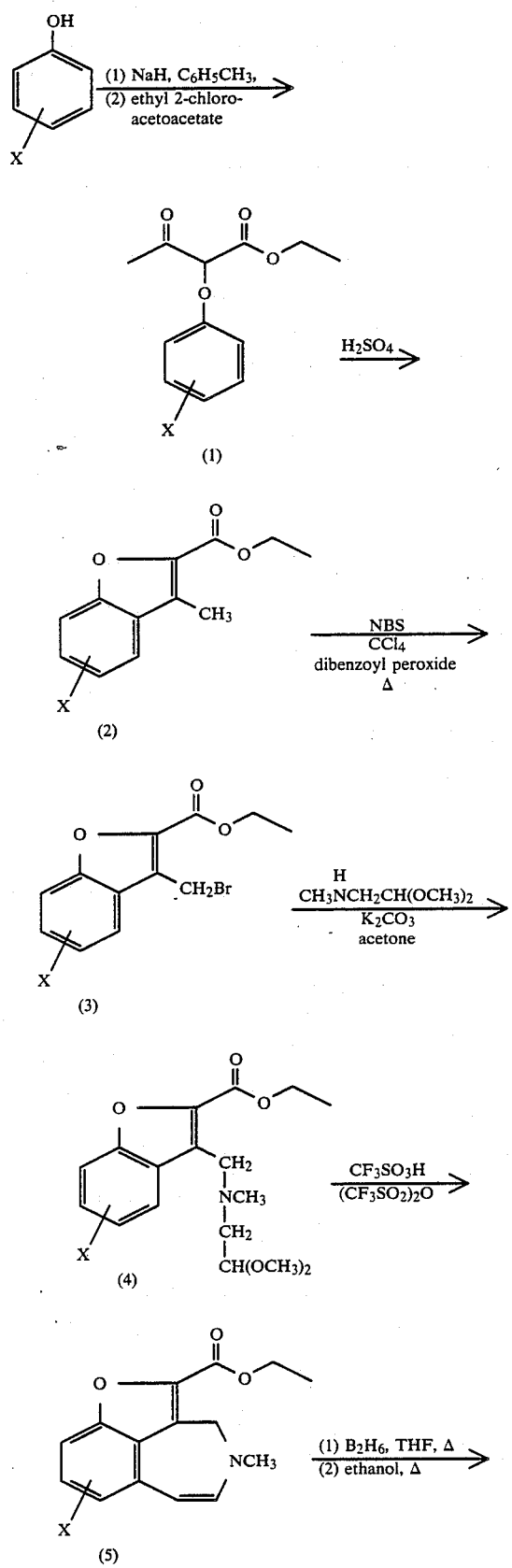

SCHEME I

-continued
SCHEME I

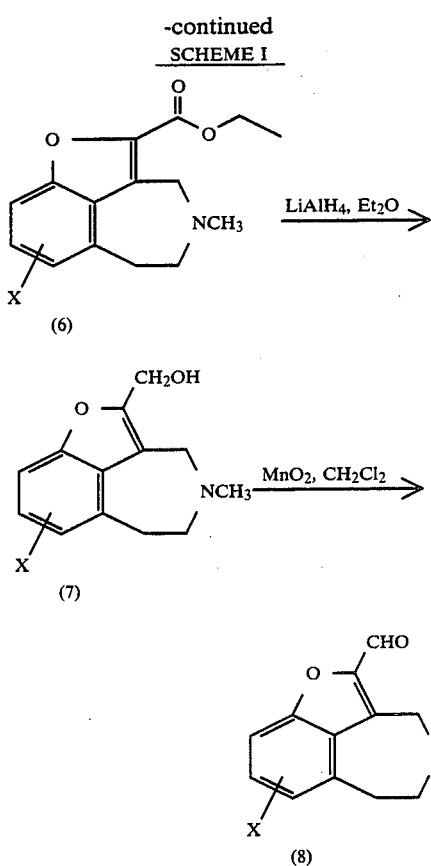

Scheme I shows the synthesis of Formula (I) related compounds in which the 2-position substituent is CO₂CH₂CH₃, CHO, and CH₂OH, which are useful as intermediates in synthesis of Formula (I) compounds. According to Scheme I, phenol or a substituted phenol is treated with a strong base such as sodium hydride in a suitable organic solvent such as toluene. The resulting sodium phenolates are heated at 40° C. to 120° C., preferably 80° C., with an $C_{1-4}$alkyl 2-haloacetoacetate, preferably ethyl 2-chloroacetoacetate to yield $C_{1-4}$alkyl 2-(phenoxy)acetoacetate compounds (1). Substituted benzofuran compounds (2) are prepared by treating compounds (1) with a strong acid, preferably sulfuric acid, at from −40° C. to 48° C., preferably 0° C.

Formula (2) compounds are treated with a halogenating agent, preferably N-bromosuccinimide (NBS), and an initiator, preferably dibenzoylperoxide, in an inert organic solvent, preferably carbon tetrachloride (CCl₄), preferably at reflux, to produce formula (3) compounds. Formula (4) compounds are prepared by dissolving formula (3) compounds in an organic solvent such as acetone and adding a suitable base, preferably potassium carbonate (K₂CO₃), and an N ($C_{1-6}$alkyl)-aminoacetaldehyde di($C_{1-4}$alkyl) acetal, preferably methylaminoacetaldehyde dimethyl acetal.

Formula (4) compounds are treated with acid, preferably trifluoromethanesulfonic acid in trifluoromethanesulfonic anhydride, to yield enamine compounds of formula (5). Formula (5) compounds are treated with a reducing agent, preferably diborane, in an inert organic solvent such as tetrahydrofuran or reduced catalytically to give benzazepine compounds of formula (6).

Thereafter, formula (6) compounds are added to a suitable reducing agent, preferably lithium aluminum hydride (LAH), in an inert solvent, preferably ethyl ether, to yield formula (7) compounds. Formula (7) compounds are treated with a suitable oxidizing agent, preferably manganese dioxide, in an inert solvent, preferably dichloromethane, to give benzazepine-2-carboxaldehyde compounds of formula (8).

SCHEME II

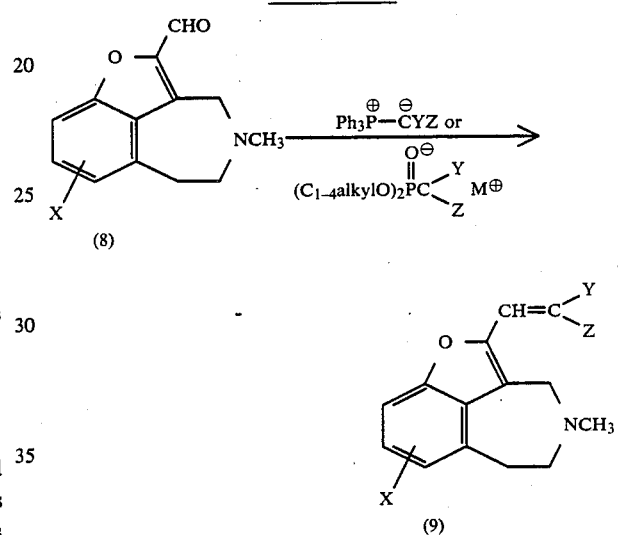

Scheme II shows formation of formula (9) compounds which are Formula (I) compounds except those in which the 2-position substituent is —CH=CH—CHO, —CH=CH—COOH, or —CH=CHCONR³R⁴. In Scheme II, X is as defined in Formula (I). The starting compounds in Scheme II are formula (8) benzazepine 2-carboxaldehydes prepared as in Scheme I. According to Scheme II, the formula (8) compound is reacted with a phosphonate or phosphonium salt in the presence of a suitable base, preferably sodium hydride, except when Y or Z is SOhd 2NR³R⁴ wherein sodium methoxide is preferred. The phosphonate or phosphonium salt is selected so that Y and Z are the same as in the desired Formula (I) compound. The metal cation (M⊕) associated with the phosphonate is derived from the base employed in this step of the synthesis. Suitable metal ions include lithium, sodium, and potassium.

Formula (I) compounds wherein the 2-position substituent is CH=CH—CHO are prepared by a process similar to Scheme II by reacting the formula (8) compound with a dialkyl phosphonoacetaldehyde dialkyl acetal, preferably diethyl phosphonoacetaldehyde diethyl acetal., followed by acid hydrolysis.

SCHEME III

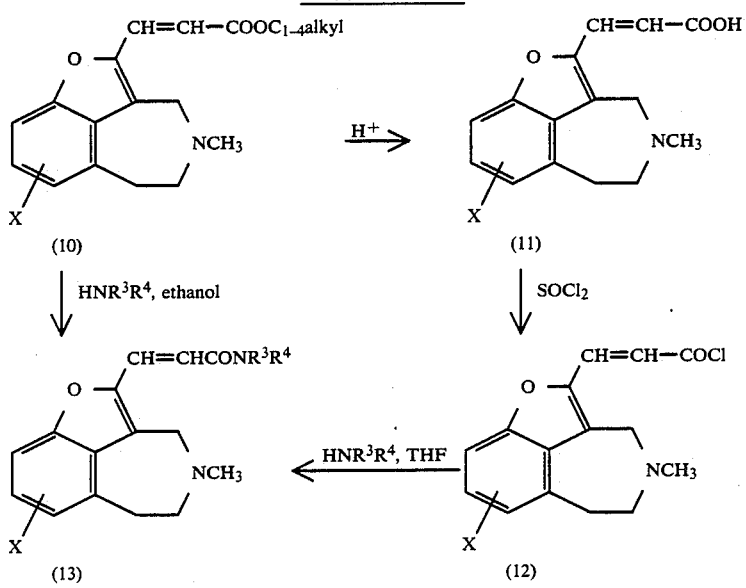

Scheme III outlines synthesis of Formula (I) compounds wherein the 2-position substituent is CH=CH—COOH or CH=CHCONR$^3$R$^4$. The formula (10) starting materials in the Scheme III process are prepared according to Scheme II and are included within the formula (9) compounds. Formula (11) compounds are formed by adding strong acid, preferably a mixture of hydrochloric and acetic acids, to Formula (10) compounds and heating the mixture to approximately 30° C. to 70° C., preferably 50° C. Compounds of formula (12) then are prepared by reacting the formula (11) compounds with a suitable halogenating agent, preferably thionyl chloride. Formula (13) compounds, which are Formula (I) compounds wherein Y or Z is CONR$^3$R$^4$ are synthesized by reacting formula (12) compounds with ammonia or substituted amines wherein R$^3$ and R$^4$ are as in the desired Formula (I) compound. Alternatively, formula (13) compounds are prepared by reacting the formula (10) esters with ammonia or a substituted amine.

Formula (1) compounds wherein R$^1$ is C$_{1-6}$alkyl are prepared by reacting formula (6) compounds with a C$_{1-6}$alkyl magnesium halide, such as methylmagnesium bromide, in a suitable solvent, such as tetrahydrofuran, followed by reaction with methanesulfonyl chloride in the presence of a suitable base, such as triethylamine.

Schemes I through III outline preparation of Formula (I) compounds in which R is methyl. Formula (I) compounds wherein R is other than methyl are formed by selecting the N-(C$_{1-6}$alkyl)aminoacetaldehyde di (C$_{1-4}$alkyl) acetal used in preparing the formula (4) compounds of Scheme I so that the nitrogen is desirably substituted. Alternatively, Formula (I) compounds wherein R is other than methyl are prepared by reacting a Formula (I) compound wherein R is methyl with an alkyl haloformate, preferably trichloroethyl chloroformate at approximately 50° C. to 100° C. to produce a trihaloalkyl carbamate. To this carbamate dissolved in a suitable organic solvent such as tetrahydrofuran is added an acid, preferably acetic acid, and a reducing agent such as zinc dust to yield a product in which R is hydrogen. This is subsequently reacted with a halo R$^7$ compound, wherein R$^7$ is C$_{2-6}$alkyl or C$_{3-5}$alkenyl, to yield Formula (I) compounds wherein R is C$_{2-6}$alkyl or C$_{3-5}$alkenyl, respectively.

The substituted phenols and C$_{1-4}$alkyl 2-haloacetoacetates used as starting materials in Scheme I are commercially available or can be synthesized from available materials by known methods. Additionally, the reactants used in Schemes I through III are available or can be synthesized from available materials by known methods.

The pharmaceutically acceptable, nontoxic, acid addition salts having the utility of the free bases of Formula (I) are formed with inorganic or organic acids by methods well known in the art. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p aminobenzoic, glutamic, benzenesulfonic, hydrochloric, hydrobromic, sulfuric, cyclohexylsulfamic, phosphoric and nitric acids.

Because the compounds of Formula (I) are α-adrenoceptor antagonists they are useful in treating cardiovascular diseases in which changes in vascular resistance are desirable, including hypertension, pulmonary hypertension, congestive heart failure, myocardial ischemia, angina pectoris, and peripheral vascular disease. Formula (I) compounds also are useful in treating benign prostatic hypertrophy, diabetes, glaucoma, ocular hypertension, obesity, disorders of gastrointestinal motility, including colonic spasm, irritable bowel syndrome, and constipation, impotence, and central nervous system disorders such as depression and senile dementia. Additionally, the invented compounds are useful in treating diseases resulting from inappropriate platelet aggregation.

The α-adrenoceptor activity of certain compounds of the present invention was determined using the following in vitro systems.

Alpha$_1$ adrenoceptor antagonist activity was determined using the rabbit aorta. Male New Zealand White rabbits (2–4 Kg) were euthanized by cervical concussion. A 4 cm portion of the thoracic aorta was removed and placed in a dish of cold (10° C.) Krebs-Hensleit solution. The tissue was cleaned of fat and connective tissue and cut into segments of approximately 3 mm in length. These segments were suspended in 10 ml tissue baths via hangers constructed of 0.25 mm tungsten wire. One hanger was fixed to a support in the bath and the other was attached via silk thread to a force displacement transducer.

Tissue segments were eguilibrated for 2 hours prior to drug testing, during which time basal tension was maintained at 2 gm. Tissues were washed at 30 minute intervals during this equilibration period. The Krebs-Hensleit solution contained cocaine (6μM) to block neuronal uptake and propranolol (1μM) to block beta adrenoceptors. Tissues were usually challenged once with norepinephrine (0.1μM) during the equilibration period to check for viability.

A cumulative concentration response curve to norepinephrine was obtained in each aortic segment. Following washout of norepinephrine, the α adrenoceptor antagonist to be tested was added to the bath. After the tissue had been in contact with the antagonist for 30-60 minutes, the norepinephrine concentration response-curve was repeated in the presence of antagonist. The tissue was then washed again, and a tenfold higher concentration of antagonist added. Following equilibration (30–60 minutes), a third norepinephrine concentration-response curve was determined in the presence of the antagonist.

The receptor dissociation constant ($K_B$) for the antagonist was determined using the relationship $$K_B = \frac{\text{Antagonist Concentration}}{\text{Dose Ratio} - 1}$$

(Furchgott, R. F., *Handbook of Experimental Pharmacology*, eds. Eichler, et al., pp. 283–335 (Springer 1972)). The $K_B$ value obtained at each antagonist concentration was averaged to obtain a mean $K_B$ for each experiment.

Alpha$_2$ adrenoceptor antagonist activity of the compounds was determined using the isolated, superfused guinea pig left atrium. Briefly, the heart is removed from a pentobarbital anesthetized male guinea pig. The left atrium is separated, dissected free of extraneous tissue and mounted in a 2 ml superfusion chamber. The tissue is paced at 30 pulse/minute and the sympathetic nerves excited at 6 minute intervals by field stimulation. The response to nerve stimulation is measured as the difference in contractile force between the basal contraction and peak contraction following a nerve stimulation. A concentration response curve for B-HT 920 (a known $\alpha_2$ agonist) is prepared by administering increasing concentrations of B HT 920 following each successive stimulation. The tissue then is superfused for thirty minutes with the α-adrenoceptor antagonist to be tested and the B-HT 920 concentration-effect curve is repeated in the presence of antagonist. Data are reported as $K_B$, defined above. Additional details of this test system are found in Hieble, J. P. and R. G. Pendleton, *Arch. Pharmacol.*, 309:217–224 (1979).

Alpha$_3$ adrenoceptor antagonist receptor activity was determined using the dog saphenous vein (DSV) as the test system. This test system has been shown a suitable preparation in which to characterize postsynaptic $\alpha_2$ ($\alpha_3$) adrenoceptors, Sullivan, A. T. and G. M. Drew, Arch. Pharmacol., 314:249-58 (1980). This test system is prepared by removing the lateral saphenous vein from an anesthetized dog and cutting the vein into segments of 4 mm in length. Segments are mounted as described for the isolated rabbit aorta.

The $\alpha_3$ adrenoceptor antagonist activity of the compounds of interest is determined by measuring shifts in the dose response curve of a specific agonist induced by the tested compounds. The $\alpha_2$, $\alpha_3$ agonist, B-HT 920, was used in testing the compounds listed in Table I.

Representative Formula (I) compounds which were tested using the above described in vitro test systems are listed in Table 1. Each of the compounds tested was found to have activity at one or more of the α adrenoceptor subtypes. Each of the compounds listed in Table 1 are Formula (Ia) compounds in which X is chloro and R is methyl unless otherwise indicated.

TABLE 1

| Y | Z |
|---|---|
| CONHCH$_3$ | CH$_3$ |
| COOC$_2$H$_5$ | C$_3$H$_7$ |
| CONH$_2$ | H |
| CH$_3$ | CH$_3$ |
| CON(CH$_3$)$_2$ | H |
| H | H |
| CONHCH$_3$ | H |
| COOC$_2$H$_5$ | H |
| COOC$_2$H$_5$ | H (R is H) |
| COOC$_2$H$_5$ | H (R is CH$_2$CH=CH$_2$) |
| COOC$_2$H$_5$ | H (R is CH$_2$CH$_3$) |
| COOC$_2$H$_5$ | CH$_3$ |
| SO$_2$CH$_3$ | H |
| COOH | H |
| COCH$_3$ | H |
| CH$_2$OH | H |
| CH$_2$OCH$_2$Ph | H |
| COCH$_2$CH$_2$CH$_3$ | H |
| COCH$_2$CH$_2$CH$_2$CH$_3$ | H |
| COCH$_2$CH$_2$Ph | H |
| CONH(CH$_3$) | CH$_2$CH$_2$OH |
| CONHCH$_2$CH$_3$ | H |
| CON(CH$_2$CH$_3$)$_2$ | H |
| CON(CH$_3$)CH$_2$Ph | H |
| CON(CH$_2$Ph)$_2$ | H |
| CO$_2$CH$_2$CH$_2$CH$_3$ | H |
| CO$_2$CH(CH$_3$)$_2$ | H |
| CO$_2$CH$_2$Ph | H |
| CO$_2$CH$_2$CH$_3$ | Ph |
| Ph | CO$_2$CH$_2$CH$_3$ |
| SO$_2$C(CH$_3$)$_3$ | H |
| CO$_2$Ph | H |
| SO$_2$N(CH$_2$CH$_3$)$_2$ | H |
| SO$_2$N(CH$_2$CH$_2$CH$_3$)$_2$ | H |
| SO$_2$N(CH$_3$)Ph | H |
| SO$_2$N(CH$_3$)CH$_2$Ph | H |
| SO$_2$N(CH$_2$Ph)$_2$ | H |

The antihypertensive activity of certain compounds of the present invention was determined using the spontaneously hypertensive rat model. The details of this in vivo test system are found in Roesler, J.M., et al., *J. Pharmacol. Exp. Ther.*, 236:1 7 (1986).

The compounds of Examples 4 and 6 reduced arterial blood pressure in spontaneously hypertensive rats following intravenous infusion of 1.5 mg/kg and 4.5 mg/kg, respectively, over 15 minutes. Diastolic and systolic blood pressures were reduced by 35-50 mmHg with durations of at least twenty minutes post-infusion.

The compounds of Examples 4 and 6 also reduced arterial blood pressure in spontaneously hypertensive rats following oral administration at doses of 20 mg/kg. Diastolic and systolic blood pressures were reduced by 22-29 mmHg with durations of at least thirty minutes.

Novel pharmaceutical compositions are obtained when the compounds are incorporated with pharmaceutical carriers into convenient dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension or solution.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds in a pharmaceutical dosage unit will be an efficacious, nontoxic quantity selected from the range of 0.01–100 mg/kg of active compound, preferably 0.1–50 mg/kg. The selected dose is administered to a human patient in need of treatment from 1-6 times daily, orally, rectally, topically, by inhalation, or injection, or continuously by infusion. Oral administration, however, is preferred because it is more convenient for the patient.

The following examples are illustrative of preparation of Formula (I) compounds. The examples are not intended to limit the scope of the invention as defined hereinabove and as claimed below.

EXAMPLE 1

Ethyl 7 Chloro 3,4,5,6tetrahydro 4-methylfuro-[4,3,2-ef][3]benzazepine 2-carboxylate (i) Ethyl 2-(4-Chlorophenoxy)acetoacetate A 60% dispersion of sodium hydride in mineral oil (40 g, 1 mol) was washed with dry petroleum ether and suspended in dry toluene (700 ml). The suspension was stirred under argon and carefully treated with a solution of 4 chlorophenol (128.6 g, 1 mol) in dry toluene (300 ml) added dropwise. The resulting suspension was stirred for 1 hour, warmed to 80° C. and treated with ethyl 2-chloroacetoacetate (165 g, 1 mol) added dropwise to maintain the internal temperature between 80–85° C. The resulting solution was stirred at 80° C. for 4 hours, cooled and carefully treated with ice. The organic phase was washed with water (3×200 ml), 10% sodium hydroxide (2×75 ml), water (200 ml) and brine (100 ml), dried with magnesium sulfate, filtered and evaporated to give an oil. The oil was distilled in vacuo [bp 126°–132° C. (0.1 mm)] to give 95 g (37%) of ethyl 2 (4-chlorophenoxy)-acetoacetate.

(ii) Ethyl 5-Chloro 3 methyl-2 benzofurancarboxylate

Ethyl 2-(4 chlorophenoxy)acetoacetate (90.3 g, 0.353 mol) was added dropwise to sulfuric acid (240 ml) stirred at 0° C. The resulting suspension was stirred at 0° C. for 3.5 hours, poured onto crushed ice and the mixture stirred for 0.5 hours. The mixture was extracted with toluene and the organic phase was washed with 5% sodium bicarbonate and water. The organic phase was dried with magnesium sulfate, filtered, evaporated and the residue recrystallized from cyclohexane to give 54.5 g (65%) of ethyl 5-chloro 3 methyl 2 benzofurancarboxylate: mp 80–82° C.

(iii) Ethyl 3-Bromomethyl 5 chloro 2-benzofurancarboxylate

A mixture of ethyl 5-chloro-3-methyl 2-benzofurancarboxylate (52.5 g, 0.22 mol), N-bromosuccinimide (39.15 g, 0.22 mol) and benzoyl peroxide (0.4 g) in carbon tetrachloride (750 ml) was stirred and refluxed for 10 hours The mixture was cooled, filtered and the filtrate evaporated to give a solid which was recrystallized from ethanol to give 52.8 g (76%) of ethyl 3-bromomethyl-5-chloro 2 benzofurancarboxylate: mp 112°–114° C.

(iv) Ethyl 5-Chloro-3-[N-(2,2-dimethoxyethyl) N-methyl)]-2-benzofurancarboxylate A mixture of ethyl 3 bromomethyl-5-chloro 2-benzofurancarboxylate (52.75 g, 0.166 mol), methylaminoacetaldehyde dimethyl acetal (19.0 g, 0.167 mol) and potassium carbonate (45 g) in dry acetone (600 ml) was stirred under argon for 30 hours, filtered and the filtrate evaporated. The residue was partitioned between ethyl ether and water and the organic phase was dried with magnesium sulfate, filtered, and evaporated to give ethyl 5-chloro-3-[N (2,2 dimethoxyethyl)-N-methyl-(aminomethyl)]-2-benzofurancarboxylate: mp 58°–60° C.

(v) Ethyl 7-Chloro 3,4-dihydro 4-methylfuro[4,3,2-ef][3]benzazepine 2-carboxylate Ethyl 5 chloro 3-[N (2,2-dimethoxyethyl)-N-methyl-(aminomethyl)]-2-benzofurancarboxylate (8.5 g, 24 mmol) was added to a mixture of trifluoromethanesulfonic anhydride (3 ml) and trifluoromethanesulfonic acid (30 ml), stirred under argon in a water bath, dropwise over 10 minutes to maintain the internal temperature between 25° –30° C. The mixture was stirred for 0.5 hours, poured into a stirred mixture of ethyl ether (750 ml) and ice water (200 ml) and the aqueous phase was carefully basified with potassium carbonate to pH 9.5. The phases were separated and the aqueous phase was extracted with ethyl ether (2×200 ml). The organic phases were combined, dried with magnesium sulfate, filtered and evaporated to give ethyl 7 chloro-3,4-dihydro-4-methylfuro[4,3,2 -ef][3]benzazepine- 2-carboxylate.

(vi) Ethyl 7-Chloro 3,4,5,6 tetrahydro 4-methylfuro[4,3,2-ef][3]benzazepine-2-carboxylate A solution of ethyl 7 chloro 3,4-dihydro 4-methylfuro[4,3,2-ef][3]benzazepine-2-carboxylate in dry tetrahydrofuran (50 ml) was added to borane in tetrahydrofuran (1 M, 100 ml, 0 1 mol) stirred under argon at 0° C. The resulting solution was refluxed for 3.5 hours, cooled, carefully treated with ethanol and evaporated. The residue was refluxed in absolute ethanol (125 ml) for 1.5 hours and the ethanol evaporated to give a residual oil which was stirred with ethyl ether (500 ml) and filtered. The filtrate was treated with hydrogen chloride and the resulting hydrochloride salt was recrystallized from absolute ethanol to give ethyl 7-chloro 3,4,5,6-tetrahydro-4-methylfuro[4,3,2-ef][3]-benzazepine 2-carboxylate hydrochloride: mp 244°–247° C.

EXAMPLE 2

7-Chloro-3,4,5,6-tetrahydro 4-methylfuro-[4,3,2-ef][3]benzazepine-2-methanol A solution of ethyl 7 chloro 3,4,5,6 tetrahydro-4-methylfuro[4,3,2-ef][3]benzazepine- 2-carboxylate (5.1 g, 17.4 mmol), prepared as in Example 1, in ethyl ether (100 ml) was added dropwise to a suspension of lithium aluminum hydride (0.85 g, 23 mmol) in ethyl ether (200 ml) stirred at 0° C. The mixture was refluxed for 2 hours, cooled and treated carefully with water (0.9 ml), 15% sodium hydroxide (0.9 ml) and water (2.7 ml). The resulting suspension was stirred for 15 minutes, filtered and the solvent evaporated to give 2.5 g (57%) of 7-chloro-3,4,5,6-tetrahydro-4-methylfuro[4,3,2-ef][3]benzazepine-2-methanol: mp 124°–128 ° C. The free base was dissolved in ethyl ether and treated with hydrogen chloride to give 7-chloro 3,4,5,6-tetrahydro 4-methylfuro[4,3,2 -ef][3]-benzazepine-2-methanol hydrochloride: mp 220°–223° C.

EXAMPLE 3

7-Chloro 3,4,5,6-tetrahydro 4-methylfuro-[4,3,2-ef][3]benzazepine-2-carboxaldehyde A solution of 7-chloro 3,4,5,6 tetrahydro 4-methylfuro[4,3,2-ef][3]benzazepine 2-methanol, prepared as in Example 2, (2.5 g, 10 mmol) in dichloromethane (100 ml) was stirred under argon with activated manganese dioxide (25 g) for 2 hours. The mixture was filtered, the filter cake washed with dichloromethane and the filtrate was evaporated to give 2.2 g (88%) of 7-chloro 3,4,5,6-tetrahydro 4-methylfuro[4,3,2-ef][3]benzazepine-2-carboxyaldehyde: mp 100°–102° C.; hydrochloride: mp >240° C. (dec).

EXAMPLE 4

7-Chloro-2-ethenyl-3,4,5,6tetrahydro 4-methylfuro[4,3,2-ef][3]benzazepine

A 60% dispersion of sodium hydride in mineral oil (1.0 g, 25 mmol) was washed with dry petroleum ether and suspended in dry dimethylformamide (50 ml) and ethyl ether. (50ml). The suspension was stirred under argon and treated with methyltriphenylphosphonium bromide (10.7 g, 30 mmol). The reaction was stirred for 45 minutes and a solution of 7 chloro 3,4,5,6 tetrahydro 4-methylfuro[4,3,2 -ef][3]benzazepine 2-carboxaldehyde, prepared as in Example 3, (4.5 g, 18 mmol) in dimethylformamide (40 ml) was added over 10 minutes. The reaction was stirred for 1 hour, poured into ice water and extracted with ethyl ether. The combined organic phases were dried with magnesium sulfate and evaporated. The residual solid was dissolved in hexane (200 ml) and cooled to −20° C. The supernatant was decanted, concentrated and treated with ethereal hydrogen chloride to give a solid which was filtered and recrystallized from acetone to give 1.5 g (30%) of 7-chloro-2-ethenyl-3,4,5,6 tetrahydro-4-methylfuro[4,3,2-ef][3]benzazepine hydrochloride: mp >250° C. (dec).

EXAMPLE 5

7-Chloro-3,4,5,6-tetrahydro-4-methyl-2-(2-methyl-1-propenyl)-furo[4,3,2-ef][3]benzazepine A solution of butyllithium in hexane (2.6 M, 1.3 ml, 3.4 mmol) was added to a suspension of isopropyltriphenylphosphonium iodide (1.5 g, 3.4 mmol) in freshly distilled tetrahydrofuran (20 ml) stirred under argon at −15° C. The mixture was stirred at −10° C. to 15° C. for 20 minutes and treated with a solution of 7 chloro-3,4,5,6-tetrahydro-4-methylfuro[4,3,2-ef][3]benzazepine- 2-carboxaldehyde, prepared as in Example 3, (0.8 g, 3.2 mmol) in tetrahydrofuran (15 ml) added dropwise over 10 minutes. The reaction was stirred for 2 hours, quenched with ethanol (3 ml) and the solvents evaporated. The residue was triturated with ethyl ether and the organic phase was evaporated. The residue was chromatographed on silica gel eluted with chloroform and the fractions containing the product were combined, evaporated, dissolved in ethyl ether and treated with hydrogen chloride to give 7-chloro-3,4,5,6-tetrahydro 4 methyl-2-1-1-propenyl)furo[4,3,2-ef][3]benzazepinehydrochloride: mp 270°–272° C. (dec).

EXAMPLE 6

Ethyl (E) 3 (7 Chloro 3,4,5,6-tetrahydro 4 methylfuro-[4,3,2-ef][3]benzazepin 2-yl)-2-propenoate A 60% dispersion of sodium hydride in mineral oil (0.82 g, 20.5 mmol) was washed with hexane was suspended in ethyl ether (210 ml). The suspension was stirred under argon and treated with triethyl phosphonoacetate (4.5 g, 22 mmol). The resulting mixture was stirred for 1 hour and treated with a solution of 7 chloro-3,4,5,6-tetrahydro-4-methylfuro[4,3,2-ef][3]benzazepine 2carboxaldehyde, prepared as in Example 3, (4.9 g, 20 mmol) in ethyl ether (250 ml). The reaction was stirred for 1.5 hours, quenched with water (25 ml) and the phases separated. The organic phase was washed with water, dried with magnesium sulfate and the solvent evaporated to give a yellow solid which was slurried with hexane and filtered to give, after recrystallization from ethanol, 5.2 g (81%) of ethyl (E)-3-(7-chloro 3,4,5,6 tetrahydro 4-methylfuro-[4,3,2-ef][3]benzazepin-2-yl)-2-propenoate: mp 118°–121° C.; hydrochloride mp >240° C. (dec).

EXAMPLE 7

Ethyl (E)-3-(7-Chloro 3,4,5,6 tetrahydrofuro-[4,3,2-ef][3]benzazepin 2-yl)-2-propenoate A solution of ethyl (E)-3-(7-chloro 3,4,5,6-tetrahydro-4-methylfuro[4,3,2-ef][3]benzazepin-2-yl)-2-propenoate, prepared as in Example 6, (1.9 g, 5.9 mmol) in 1,2-dichloroethane (75 ml) was treated with 2,2,2-trichloroethyl chloroformate (3.75 g, 17.7 mmol). The resulting suspension was refluxed for 7 hours, the solvent evaporated and the residue dissolved in hot ethanol (200 ml). The ethanolic solution was concentrated to 70 ml and cooled to give 2.1 g (73%) of the trichloroethyl carbamate: mp 154°–155° C.

A solution of the trichloroethyl carbamate (2.0 g, 4.16 mmol) in tetrahydrofuran (70 ml) and glacial acetic acid (10 ml) was treated with activated zinc powder (5.0 g) and the resulting suspension was stirred at room temperature for 1 hour. The mixture was filtered, concentrated, and the residue was partitioned between 5% sodium bicarbonate and dichloromethane. The organic phase was dried with magnesium sulfate and evaporated. The residue was dissolved in ethyl ether and treated with hydrogen chloride and recrystallized from ethanol to give 0.45 g (35%) of ethyl (E)-3-(7 chloro 3,4,5,6-tetrahydrofuro[4,3,2-ef][3]benzazepin-2-yl)-2-propenoate hydrochloride: mp >285° C. (dec).

EXAMPLE 8

Ethyl (E)-3-[7-Chloro 3,4,5,6-tetrahydro-4-(2 propenyl)-furo[4,3,2-ef][3]benzazepin-2-yl]-2-propenoate A solution of ethyl (E)-3-(7-chloro 3,4,5,6-tetrahydrofuro[4,3,2-ef][3]benzazepin 2-yl)-2-propenoate (0.17 g, 0.56 mmol), prepared as in Example 7, in dry acetone (30 ml) was stirred and treated with potassium carbonate (0.5 g) and allyl iodide (0.10 g, 0.58 mmol). The reaction was stirred for 16 hours, filtered, evaporated, and the residue partitioned between ethyl ether and water. The organic phase was dried with magnesium sulfate and treated with hydrogen chloride to give 0.05 g (25%) of ethyl (E)-3-[7-chloro 3,4,5,6-tetrahydro-4-(2-propenyl)furo[4,3,2-ef][3]benzazepin-2-yl]-2-propenoate: mp >240° C. (dec).

EXAMPLE 9

Ethyl (E)-3 (7-Chloro 3,4,5,6 tetrahydro 4 methylfuro-[4,3,2-ef](3]benzazepin-2-yl)-2-methyl-2-propenoate Using the general procedure of Example 6, replacing triethyl phosphonoacetate with triethyl 2-phosphonopropanoate gave ethyl (E) 3-(7-chloro-3,4,5,6-tetrahydro-4-methylfuro[4,3,2-ef][3]benzazepin-2-yl)-2-methyl-2 propenoate hydrochloride: mp 254°–256° C. (dec).

EXAMPLE 10

Ethyl (E) 3-(7 Chloro 3,4,5,6 tetrahydro-4-methylfuro-[4,3,2-ef][3]benzazepin-2-yl)-2-propyl-2-propenoate Using the general procedure of Example 6, replacing triethyl phosphonoacetate with triethyl 2-phosphonopentanoate gave, after fractional recrystallization from ethanol, 0.10 g (20%) of ethyl (E)-3-(7-chloro-3,4,5,6 tetrahyiro-4 methylfuro[4,3,2 -ef][3]benzazepin 2-yl)-2-propyl-2-propenoate hydrochloride: mp >240° C. (dec).

EXAMPLE 11

Ethyl (Z) 3-(7-Chloro 3,4,5,6 tetrahydro-4-methylfuro-[4,3,2-ef][3]benzazepin-2-yl)-2-fluoro-2-propenoate A solution of diethylaluminum chloride in hexane (1 M, 4.4 mmol, 4.4 ml) was added to a stirred suspension of copper (I) bromide (58 mg, 0.2 mmol) and activated zinc dust (0.4 g, 6 mmol) in freshly distilled tetrahydrofuran (35 ml). The mixture was cooled to −30° C., stirred vigorously, and treated with a solution of 7 chloro 3,4,5,6 tetrahydro 4-methylfuro[4,3,2 ef][3]benzazepine-2-carboxaldehyde (1.0 g, 4.0 mmol), prepared as in Example 3, and ethyl bromofluoroacetate (0.74 g, 4.0 mmol) in tetrahydrofuran (15 ml) added dropwise over 30 minutes. The reaction temperature was allowed to rise slowly to 0° C. over a period of 40 minutes. The resultinq suspension then was warmed to room temperature and stirred for 1.5 hours. Ethyl ether was added to bring the total volume to 250 ml and the mixture was treated with water (10 ml) and 5% sodium bicarbonate (15 ml). The mixture was filtered and the organic phase was washed with water and brine, dried with magnesium sulfate and evaporated. The residue was flash chromatographed on silica eluted with 10% ethanol in dichloromethane to give 0.8 q (56%) of a mixture of isomers of ethyl 3(7-chloro-3,4,5,6-tetrahydro-4-methylfuro[4,3,2-ef][3]benzazepin-2-yl)-2-fluoro-3-hydroxypropanoate: mp 130-140° C.

A solution of ethyl 3-(7-chloro-3,4,5,6-tetrahydro 4-methylfuro[4,3,2-ef][3]benzazepin-2-yl)-2-fluoro-3-hydroxypropanoate (0.65 g, 1.8 mmol) and triethylamine (3 ml) in dry dichloromethane (35 ml) was stirred at -20° C. and a solution of methanesulfonyl chloride (0.21 g, 1.9 mmol) in methylene chloride (5 ml) was added dropwise over a period of 2–3 minutes. The reaction was stirred at −20° C. for 20 minutes, and then at room temperature for 2 hours. The mixture was treated with 5% sodium bicarbonate (5 ml) and the organic phase was dried with magnesium sulfate and evaporated. The residue was flash-chromatographed on silica eluted with 10% ethanol in dichloromethane to give 0.33 g (52%) of ethyl (Z)-3-(7-chloro-3,4,5,6-tetrahydro-4-methylfuro[4,3,2-ef][3]benzazepin-2-yl)-2-fluoro-2-propenoate: mp 138°–140° C.

EXAMPLE 12

Ethyl (Z)-2-Chloro 3 (7 chloro 3,4,5,6-tetrahydro 4-methylfuro[4,3,2-ef][3]benzazepin-2-yl)-2-propenoate Ethyl (Z)-2-Chloro-3(7-chloro-3,4,5,6-tetrahydro-4-methylfuro[4,3,2,-ef][3]benzazepin-2-yl)-2-propenoate A 50% dispersion of sodium hydride in mineral oil (92 mg, 1.9 mmol) was washed under argon with hexane and suspended in dry 1,2-dimethoxyethane (1 ml). The suspension was stirred under argon, cooled to 10° C., and treated with a solution of triethyl phosphono 2-chloroacetate (450 mg, 1.7 mmol) in dry 1,2 dimethoxyethane (2 ml). The mixture was warmed to 20° C., treated with a solution of 7 chloro-3,4,5,6-tetrahydro 4-methylfuro[4,3,2-ef][3]benzazepine-2-carboxaldehyde (435 mg, 1.7 mmol), prepared as in Example 3, in 1,2-dimethoxyethane (4 ml) and stirred for 2.5 hours. The reaction was poured into ice and the mixture was extracted with dichloromethane. The organic phase was dried with magnesium sulfate and evaporated. The residue was chromatographed on sllica eluted with 3% methanol in chloroform to give two fractions. The individual fractions were further purified by reverse phase thin layer chromatography on C-18 silica eluted with 10% water in methanol to give the pure E and Z isomers. These were separately dissolved in methanol and treated with ethereal hydrogen chloride to give 19 mg (3.0%) of ethyl E) 2-chloro 3 (7 chloro 3,4,5,6 tetrahydro-4-methylfuro[4,3,2 -ef][3]benzazepin 2yl)- 2-propenoate hydrochloride: mp 221 222° C (dec) and 65 mg (11%) of ethyl (Z) 2-chloro 3 (7-chloro 3,4,5,6 tetrahydro 4-methylfuro-[4,3,2-ef][3]benzazepin-2-yl)-2-propenoate hydrochloride: mp >255° C. (dec).

EXAMPLE 13

Ethyl (Z)-2-Bromo-3-(7-chloro 3,4,5,6-tetrahydro-4-methylfuro[4,3,2-ef][3]benzazepin-2yl)-2-propenoate A 50% suspension of sodium hydride in mineral oil (0.1 g, 2 mmol) was washed under argon with hexane and suspended in dry 2-ethoxyethyl ether (2 ml). The suspension was stirred under argon, treated dropwise with a solution of triethyl phosphonoacetate (450 mg, 2 mmol), and stirred until hydrogen evolution ceased. The resulting mixture was treated with bromine (320 mg, 2 mmol) added dropwise at a rate to keep the internal temperature below 25° C. The mixture was warmed to 40° C. for a brief period, cooled to 10° C., treated with sodium hydride (0.1 g, 2 mmol), and stirred until hydrogen evolution ceased and the internal temperature reached 20° C. The resulting mixture was stirred and treated with a solution of 7-chloro 3,4,5,6 tetrahydro 4 methylfuro-[4,3,2-ef][3]benzazepine 2-carboxaldehyde (0.05 g, 2.0 mmol), prepared as in Example 3, in 2-ethoxyethyl ether (4 ml) added dropwise at a rate to keep the internal temperature below 30° C. The reactiun was stirred for 2 hours, treated with water (60 ml) and extracted with ethyl ether. The organic phase was dried with magnesium sulfate, evaporated and chromatographed on silica eluted with 3:1:1 toluene ethyl acetate ethanol. Fractions containing the product were pooled, evaporated, and treated with hydrogen chloride. The hydrochloride was recrystallized from ethanol to give 268 mg (34%) of ethyl (Z) 2-bromo 3 (7 chloro 3.4,5,6 tetrahydro 4 methylfuro-[4,3,2 ef][3]benzazepin 2 yl)-2-propenoate: mp 245° C. (dec).

EXAMPLE 14

(E)-3 (7 Chloro 3,4,5,6 tetrahydro-4 methylfuro-[4,3,2-ef][3]benzazepin-2 Y2-yl)-2-propenoic Acid Ethyl (E) 3-(7-chloro 3,4,5,6 tetrahydro-4-methylfuro[4,3,2 ef][3]benzazepin 2-yl)-2-propenoate (0.4 g, 1.25 mmol), prepared as in Example 6, was suspended in 6N hydrochloric acid (10 ml) and acetic acid (10 ml) and the mixture was stirred at 50° C. for 18 hours; cooled and filtered to give 0.3 g (75%) of (E)-3-(7-chloro-3,4,5,6-tetrahydro-4-methylfuro[4-methylfuro[4,3,2-ef][3]benzazepin-2-yl)-2-propenoic acid hydrochloride: mp >290° C. (dec).

EXAMPLE 15

Methyl (E)-3-(7-Chloro 3,4,5,6-tetrahydro-4-methylfuro-[4,3,2 ef][3]benzazepin 2-yl)-2-propenoate Using the general procedure of Example 6, replacing triethyl phosphonoacetate with methyl diethylphosphonoacetate gave methyl (E)-3 (7 chloro-3,4,5,6-tetrahydro-4-methylfuro[4,3,2-ef][3]benzazepin-2-yl)-2-propenoate hydrochloride: mp 252°–253° C. (dec).

EXAMPLE 16

(E)-3-(7 Chloro-3,4,5,6 tetrahydro-4-methylfuro-[4,3,2-ef][3]benzazepin-2-yl)-2-propenamide (E)-3-(7-Chloro-3,4,5,6 tetrahydro-4-methylfuro-[4,3,2 ef][3]benzazepin 2-yl) 2 propenoic acid (0.8 g, 2.4 mmol), prepared as in Example 14, and thionyl chloride (15 ml) were mixed, stirred under argon, and refluxed for 1 5 hours. The thionyl chloride was evaporated to give (E) 3 (7-chloro-3,4,5,6-tetrahydro 4-methylfuro[4,3,2- (ef][3]benzazepin 2-yl) 2-propenoyl chloride hydrochloride.

The propenoyl chloride was suspended in tetrahydrofuran (50 ml), stirred, cooled to -5° C., and treated with a stream of ammonia for 15 minutes. The mixture was allowed to warm to room temperature and stirred for 0.5 hours. The solvent was evaporated and the residue partitioned between dichloromethane and water. The organic phase was dried with magnesium sulfate, evaporated and the residue slurried in ethanol and filtered. The filter cake was dissolved in chloroform and treated with hydrogen chloride to qive 0.25 g (33%) of (E)-3(7-chloro-3,4,5,6-tetrahydro- 4-methylfuro[4,3,2-ef]-[3]benzazepin-2-yl)-2-propenamide hydrochloride: mp >260° C.

EXAMPLE 17

(E)-3-(7-Chloro-3,4,5,6-tetrahydro-4-methylfuro[4,3,2-ef]-[3]benzazepin-2-yl)-N-methyl-2-propenamide Ethyl (E)-3-(7-chloro-3,4,5,6-tetrahydro-4-methylfuro[4,3,2-ef][3]benzazepin-2-yl)-2-propenoate (0.5 g, 1.6 mmol), prepared as in Example 6, was added to a solution of absolute ethanol (30 ml) saturated with methylamine and the flask was sealed. After 18 hours, the solvent was evaporated and the residue was recrystallized from absolute ethanol to give 0.35 g (65%) of (E)-3-(7-chloro-3,4,5,6-tetrahydro-4-methylfuro[4,3,2-ef][3]-benzazepin-2yl)-N-methyl-2-propenamide: mp >280° C. (dec).

EXAMPLE 18

(E)-3-(7-Chloro-3,4,5,6-tetrahydro-4-methylfuro[4,3,2-ef)[3]benzazepin-2-yl) N,N-dimethyl-2-propenamide Using the procedure of Example 16, replacing ammonia with dimethylamine gave (E)-3-(7-chloro-3,4,5,6-tetrahydro 4-methylfuro[4,3,2-ef][3]benzazepin-2-yl)-N,N-dimethyl-2-propenamide hydrochloride: mp 258–260° C.

EXAMPLE 19

(E)-3-(7-Chloro 3,4,5,6-tetrahydro 4-methylfuro[4,3,2-ef][3]benzazepin-2-yl)-N,2-dimethyl-2-propenamide (i) (E) 3-(7-Chloro 3,4,5,6-tetrahydro 4-methylfuro[4,3,2-ef][3]benzazepin-2-yl)2-methyl-2-propenoic Acid Using the general procedure of Example 14, replacing ethyl (E)-3 (7 chloro 3,4,5,6-tetrahydro-4-methylfuro[4,3,2-ef][3]benzazepin-2-yl)-2propenoate with ethyl (E) 3-(7-chloro-3,4,5,6-tetrahydro-4-methylfuro-[4,3,2-ef][3]benzazepin-2-yl)-methyl-2-propenoate, prepared as in Example 9, gave a quantitative yield of (E) 3 (7-chloro-3,4,5,6-tetrahydro 4-methylfuro-[4,3,2-ef][3]benzazepin-2-yl) 2-methyl-2-propenoic acid hydrochloride: mp >260° C. (dec).

(ii) (E)-3-(7-Chloro 3,4,5,6-tetrahydro 4-methyl-furo[4,3,2-ef][3]benzazepin-2-yl)-N,2-dimethyl-2-propenamide Using the general procedure of Example 16, replacing (E)-3-(7-chloro-3,4,5,6tetrahydro-4-methylfuro[4,3,2-ef][3]benzazepin-2-yl)-2-propenoic acid with (E)-3-(7-chloro-3,4,5,6-tetrahydro-4-methylfuro-[4,3,2-ef][3]benzazepin-2-yl)-2-mehyl-2-propenoic acid and ammonia with methylamine gave, after recrystallization from ethanol, 0.15 g (50%) of (E)-3-(7-chloro-3,4,5,6-tetrahydro-4-methylfuro-[4,3,2-ef][3]benzazepin-2-yl)-N, 2-dimethyl-2-propenamide hydrochloride: mp >296° C. (dec).

EXAMPLE 20

(E)-3-(7-Chloro-3,4,5,6-tetrahydro-4-methylfuro-[4,3,2-ef][3]benzazepin-2-yl)-2-propenenitrile Using the general procedure of Example 6, replacing triethyl phosphonoacetate with diethyl cyanomethylphosphonate qave (E)-3-(7 chloro-3,4,5,6-tetrahydro-4-methylfuro[4,3,2-ef][3]benzazepin-2-yl)-2-propenenitrile hydrochloride: mp 259–260° C. (dec).

EXAMPLE 21

(E) 4 (7Chloro 3,4,5,6-tetrahydro 4-methylfuro-[4,3,2ef][3]benzazepin-2-yl)-3-buten-2-one A solution of 7 chloro-3,4,5,6-tetrahydro 4-methylfuro[4,3,2-ef][3]benzazepine 2 carboxaldehyde (423 mg, 1.3 mmol), prepared as in Example 3, in absolute ethanol (20 ml) was stirred under argon and treated with a solution of 1-triphenylphosphoranylidene 2-propanone (300 mg, 1.2 mmol) in absolute ethanol (10 ml). The reaction was stirred for 17 hours, evaporated, and chromatographed on silica gel eluted with 5% methanol in ethyl acetate. Fractions containing the product were pooled, evaporated, and the residue was dissolved in methanol and treated with ethereal hydrogen chloride to give 75 mg of (E)-4-(7-chloro 3,4,5,6 tetrahydro 4-methylfuro[4,3,2-ef][3]benzazepin- 2-yl)-3-buten-2-one hydrochloride: mp 160–161° C.

EXAMPLE 22

(E)-7-Chloro-3,4,5,6-tetrahydro-4-methyl 2[2-(methylsulfonyl)ethenyl]furo[4,3,2-ef][3]benzazepin Using the general procedure of Example 6, replacing triethyl phosphonacetate with dimethyl methylsulfonylmethylphosphonate gave (E)-7-chloro-3,4,5,6-tetrahydro-4-methyl-2-[2-(methylsulfonyl)ethenyl]-furo[4,3,2-ef][3]benzazepine: mp 113–115° C.

EXAMPLE 23

(E)-2-(7 Chloro-3,4,5,6-tetrahydro 4-methylfuro[4,3,2-ef][3]benzazepin-2-yl) N,N-dimethyl-ethenesulfonamide A solution of 7-chloro 3,4,5,6 tetrahydro 4-methylfuro[4,3,2-ef][3]benzazepine 2-carboxaldehyde (337 mg, 1.3 mmol), prepared as in Example 3, and diethyl [[dimethyl(amino)sulfonyl]methyl]phosphonate (382 mq, 1.5 mmol) in dry methanol (10 ml) was stirred under arqon and treated with methanolic sodium methoxide prepared by dissolving sodium (30 mq, 1.3 mmol) in methanol (0.75 ml). The reaction was stirred for 5 hours and treated dropwise with water (10 ml) to give a solid which was filtered and recrystallized from methanol to give (E) 2 (7 chloro-3,4,5,6-tetrahydro 4-methylfuro-[4,3,2-ef][3]benzazepin 2-yl)-N,N-dimethylethenesulfonamide: mp 171°–171.5° C.

EXAMPLE 24

Diethyl (E)-[2-(7-Chloro-3,4,5,6-tetrahydro-4 methylfuro-

[4,3,2 ef][3]benzazepin 2-yl)ethenyl]phosphonate

Using the general procedure of Example 6, replacing triethyl phosphonoacetate with tetraethylmethylenebisphosphonate gave diethyl (E)-[2-(7-chloro-3,4,5,6 tetrahydro-4 methylfuro[4,3,2 ef][3]benzazepin2yl)ethenyl]phosphonate hydrochloride: mp 186–187° C.

EXAMPLE 25

Ethyl (E)-3-(7-Cyano-3,4,5,6-tetrahydro 4-methylfuro-[4,3,2-ef][3]benzazepin-2-yl)-2-propenoate Using the general procedure of Example 1, replacing 4-chlorophenol with 4 bromophenol qives ethyl 7 bromo 3,4,5,6 tetrahydro 4-methylfuro[4,3,2 -ef][3]-benzazepine2-carboxylate. The bromo compound is heated with cuprous cyanide in dimethylformamide to give ethyl 7-cyano-3,4,5,6 tetrahydro-4-methylfuro[4,3,2-ef][3]-benzazepine 2-carboxylate.

Using the general procedures of Examples 2, 3, and 6, the cyano-carboxylate is reduced with lithium borohydride, oxidized with manganese dioxide and condensed with triethyl phosphonoacetate to give ethyl (E)-3-(7-cyano-3,4,5,6-tetrahydro-4 methylfuro[4,3,2-ef][3]-benzazepin 2-yl) 2-propenoate.

EXAMPLE 26

Ethyl (E)-3-(7-Fluoro-3,4,5,6-tetrahydro-4-methylfuro-[4,3,2-ef][3]benzazepin 2 yl)-2-propenoate Using the general procedure of Example 1, replacing 4 chlorophenol with 4 fluorophenol gives ethyl 7 fluoro 3,4,5,6 tetrahydro 4 methylfuro[4,3,2-ef][3]benzazepine-2-carboxylate.

Using the qeneral procedures of Example 2, 3, and 6, ethyl 7-fluoro-3,4,5,6-tetrahydro 4-methylfuro-[4,3,2-ef][3]benzazepine-2-carboxylate is reduced, oxidized, and condensed with triethyl phosphonoacetate to give ethyl (E) 3 (7-fluoro 3,4,5,6-tetrahydro 4-methylfuro-[4,3,2-ef][3benzazepin-2-yl)-2-propenoate.

EXAMPLE 27

(Z)-3-(7-Chloro-3,4,5,6-tetrahydro-4-methylfuro-[4,3,2-ef][3]benzazepin-2-yl)-2-propenoate A solution of methyl bis(2,2,2-trifluoroethyl)phosphonoacetate (0.8 g, 2.5 mmol) and 18-crown 6 (0.66 g, 2.5 mmol) in dry tetrahydrofuran (35 ml) at -78° C was stirred and treated with a solution of potassium bis(-trimethylsilyl)amide (0.5 M, 5.0 ml, 2.5 mmol) in toluene A solution of 7-chloro 3,4,5,6-tetrahydro 4-methylfuro[4,3,2-ef][3]benzazepine 2-carboxaldehyde (0.62 g, 2.5 mmol), prepared as in Example 3, in dry tetrahydrofuran (10 ml) was added dropwise over a period of 5 minutes. The reaction was stirred for 0.5 hours, warmed to room temperature for 45 minutes, and quenched with saturated ammonium chloride (4 ml). The resultinq suspension was diluted with ethyl ether (100 ml) and extracted with water (2×10ml). The organic layer was dried over sodium sulfate and evaporated to qive an oil, which was purified by flash chromatography on silica eluted with 5% ethanol in dichloromethane to yield 0.39 g (52%) of methyl (Z)-3-(7 chloro 3,4,5,6-tetrahydro 4-methylfuro[4,3,2-ef][3]benzazepin-2-yl)-2-propenoate as a eolorless oil; hydrochloride: mp >225° C. (dec).

EXAMPLE 28

Ethyl (E) 3 (7 Chloro 4-ethyl-3,4,5,6 tetrahydrofuro-[4,3,2-ef][3]benzazepin-2-yl)-2-propenoate (i) Ethyl 7-chloro 3,4,5,6 tetrahydrofuro-[4,3,2-ef][3]benzazepine-2-carboxylate Using the general procedure of Example 7, replacing ethyl (E)-3-(7-chloro-3,4,5,6-tetrahydro-4-methylfuro[4,3,2-ef][3]benzazepin-2-yl)-2-propenoate with ethyl 7 chloro-3,4,5,6-tetrahydro-4-methylfuro-[4,3,2-ef][3]benzazepine-2-carboxylate, prepared as in Example 1, gave an 83% yield of the desired 2,2,2-trichloroethyl carbamate: mp 154–156° C.

The carbamate was treated with zincacetic acid to give a 74% yield of ethyl 7 chloro-3,4,5,6-tetrahydrofuro[4,3,2-ef][3]benzazepine-2-carboxyylate: mp 112–115° C.

(ii) 7-Chloro 3,4,5,6 tetrahydro-4-ethylfuro[4,3,2-ef][3]benzazepine-2-methanol A solution of ethyl 7 chloro 3,4,5,6tetrahydrofuro-[4,3,2-ef][3]benzazepine 2-carboxylate (0.75 g, 2.7 mmol) and triethylamine (3 ml) in dry tetrahydrofuran (25 ml) was stirred and treated with acetyl chloride (1.0 g, 12.7 mmol) in one portion. After 20 minutes, the reaction mixture was filtered, evaporated, and the residue slurried in acetone. Filtration gave 0.54 g (75%) of ethyl 4 acetyl-7-chloro-3,4,5,6-tetrahydrofuro[4,3,2-ef][3]benzazepine 2-carboxylate: mp 154–156° C.

A soluton of ethyl 4-acetyl-7-chloro-3,4,5,6-tetrahydrofuro[4,3,2 ef][3]benzazepine-2carboxylate (0.54 g 1.67 mmol) in tetrahydrofuran (25 ml) was added dropwise to a stirred suspension of lithium aluminum hydride (0.126 g, 3.3 mmol) in ethyl ether (25 ml). Following standard work up, the product was purified by preparative thin layer chromatoqraphy on silica eluted with 10% ethanol in dichloromethane to qive 0.16 g (22%) of 7-chloro 4-ethyl 3,4,5,6 tetrahydrofuro-]benzazepine-2-methanol as a colorless oil.

(iii) 7-Chloro 4 ethyl-3,4,5,6-tetrahydrofuro-4,3,2-ef][3]benzazepine-2-carboxaldehyde Using the general procedure of Example 3, replacing 7-chloro 3,4,5,6 tetrahydro 4-methylfuro-[4,3,2-ef][3]benzazepine-2-methanol with 7-chloro-4-ethyl-3,4,5,6-tetrahydrofuro[4,3,2-ef][3]benzazepine-2-methanol yields 0.16 g (100%) of 7-chloro-4-ethyl-3,4,5,6-tetrahydrofuro[4,3,2-ef][3]benzazepine-2-carboxaldehyde: mp 60–62° C.

(iv) Ethyl 3 (7 Chloro 4-ethyl-3,4,5,6-tetrahydrofuro[4,3,2-ef][3]benzazepin-2yl)-2-propenoate Using the general procedure of Example 6, replacing 7-chloro 3,4,5,6-tetrahydro 4 methylfuro-[4,3,2-ef][3]benzazepine 2carboxaldehyde with 7-chloro 4- ethyl 3,4,5,6 -tetrahydrofuro[4,3,2 ef][3]-benzazepine-2-carboxaldehyde yields 0.11 g (55%) of ethyl (E) 3-(7 chloro 4 ethyl-3,4,5,6 tetrahydrofuro[4,3,2 ef][3]benzazepin-2-propenoate: mp 100°–102° C.;

EXAMPLE 29

(E)-3-(7-chloro-3,4,5,6 tetrahydro-4-methylfuro-[4,3,2 ef][3]benzazeoin-2-y1)-N-methyl-2-(2)hydroxyethyl)-2-propenamide Using the general procedure of Example 6, replacing triethyl phosphonoacetate with triethyl hydroxy-2-phosphonobutyrate gives ethyl (E) 3 (7chloro-3,4,5,6 tetrahydro 4-methylfuro[4,3,2 ef][3]-benzazepin-2-yl)-2-(2-hydroxyethyl)-2-propenoate. Using the general procedure of Example 17, replacing ethyl (E)-3 (7 chloro 3,4,5,6-tetrahydro 4methylfuro[4,3,2-ef-]-[3-benzazepin-2-yl) 2-propenoate with ethyl (E)-3-(7-chloro-3,4,5,6 tetrahydro 4-methylfuro[4,3,2-ef][3]bennzazepin 2-yl)-2(2hydroxyethyl)-2propenoate gives (E)-3 (7-chloro 3,4,5,6-tetrahydro 4 methylfuro[4,3,2 ef][3]benzazepin-2-yl)-N-methyl 2-(2-hydroxyethyl)-2-propenamide.

EXAMPLE 30

Ethyl (E) 3-(9-Chloro-3,4,5,6-tetrahydro 4-methylfuro-[4,3,2-ef][3]benzazepin-2-yl)-2-propenoate Using the general procedure of Example 1, replacing 4 chlorophenol with 2 chlorophenol gives ethyl 9-chloro 3,4,5,6 tetrahydro 4 methylfuro[4,3,2-ef][3]-benzazepine 2carboxylate.

Using the general procedures of Examples 2, 3, and 6, ethyl 9 chloro 3,4,5,6 tetrahydro-4-methylfuro-4,3,2-ef][3]benzazepine-2-carboxylate is reduced, oxidized, and condensed with triethyl phosphonoacetate to give ethyl (E)-3 (9 chloro 3,4,5,6 tetrahydro 4-methylfuro[4,3,2 ef][3]benzazepin-2-yl)-2-propenoate.

EXAMPLE 31

(E)-3 (7 Chloro 3,4,5,6 tetrahydro 4-methylfuro-[4,3,2-ef][3]benzazepin-2yl) 2-propen-1-ol Diisobutylaluminum hydride in toluene (1.5 M, 5 ml, 7.5 mmol) was added to a solution of ethyl (E) 3-(7 chloro 3,4,5,6 tetrahydro 4-methylfuro-[4,3,2 ef][3]benzazepin 2-yl) 2propenoate, prepared as in Example 6, (1g 2.9 mmol) in toluene (50ml) stirred at 0° C. under argon. The mixture was allowed to stir for two hours at 25° C., quenched with water, and extracted with toluene. The organic phase was dried with magnesium sulfate and concentrated in vacuo to give product which was treated with hydrogen chloride to give (E) 3-(7-chloro-3,4,5,6-tetrahydro 4-methylfuro[4,3,2-ef][3benzazepin-2-yl)-2-propen-1-ol hydrochloride: mp 140°–142° C.

EXAMPLE 32

7,9-Dichloro 2-ethenyl-3,4,5,6-tetrahydro 4-methylfuro-[4,3,2-ef][3]benzazepine

Using the general procedure of Example 1, replacing 4-chlorophenol with 2,4-dichlorophenol yields ethyl 7,9-dichloro-3,4,5,6-tetrahydro-4-methylfuro-[4,3,2-ef][3]benzazepine-2-carboxylate with ethyl 7,9-dichloro-3,4,5,6-tetrahydro-4-methylfuro[4,3,2-ef][3]-benzazepine-2-carboxylate yields 7,9-dichloro-3,4,5,6-tetrahydro-4-methylfuro[4,3,2-ef][3]benzazepine-2-methanol.

Using the general procedure of Example 3, replacing 7 chloro 3,4,5,6-tetrahydro 4-methylfuro-[4,3,2-ef][3]benzazepine-2-methanol with 7,9-dichloro-3,4,5,6-tetrahydro-4-methylfuro[4,3,2 ef][3]benzazepine 2methanol yields 7,9 dichloro 3,4,5,6-tetrahydro 4-methylfuro[4,3,2 ef][3]benzazepine-2-carboxaldehyde.

Using the general procedure of Example 4, replacing 7-chloro 3,4,5,6 tetrahydro 4 methylfuro-[4,3,2 ef][3-]benzazepine 2 carboxaldehyde with 7,9-dichloro 3,4,5,6 tetrahydro 4 methylfuro[4,3,2 ef][3]benzazepine 2-carboxaldehyde yields 7,9-dichloro-2-ethenyl 3,4,5,6-tetrahydro-4 methylfuro[4,3,2 ef][3]benzazepine.

EXAMPLE 33

Ethyl (E)-3 (7-Chloro 3,4,5,6-tetrahydro-4-methylfuro-[4,3,2-ef][3]benzazepin-2-yl)-2-yl)-2-phenyl-2-propenoate Ethyl (Z)-3-(7-Chloro-3,4,5,6-tetrahydro-4-methylfuro-[4,3,2-ef][3]benzazepin-2-yl)-2-phenyl-2-propenoate Using the general procedure of Example 6, replacing triethyl phosphonoacetate with triethyl phosphono 2 phenylacetate gave:

ethyl (E) 3-(7 chloro 3,4,5,6-tetrahydro-4-methylfuro-[4,3,2-ef][3]benzazepin-2-yl)-2-phenyl-2-propenoate [4,3,2-ef][3]benzazepin-2yl) 2-phenyl-2-propenoate hydrochloride: mp 239°–240° C. and ethyl (Z) 3 (7 chloro 3,4,5,6-tetrahydro 4-methyl-furo-[4,3,2-ef][3]benzazepin-2-yl)-2-phenyl-2-propenoate hydrochloride: mp 242°–243° C.

EXAMPLE 34

7-Chloro 3,4,5,6 tetrahydro 4 methyl-2 (1-methylethenyl)-furo[4,3,2-ef][3]benzazepine Methylmagnesium bromide in tetrahydrofuran (3M, 45 mmol) is added to a solution of ethyl 7-chloro-3,4,5,6-tetrahydro-4-methylfuro[4,3,2-ef][3]benzazepine-2-carboxylate, prepared as in Example 1, (10 mmol) in tetrahydrofuran (60 ml) stirred under arqon. The mixture is stirred for 1 hour, treated with water and extracted with ethyl ether. The orqanic phase is dried with maqnesium sulfate and concentrated to give an oil which is chromatographed on silica gel eluted with methanol-methylene chloride to give 7-chloro 3,4,5,6-tetrahydro-α,α,4-trimethylfuro-[4,3,2 ef][3]benzazepine 2-methanol.

Triethylamine (2 ml) and methanesulfonyl chloride (10 mmol) are added to a solution of 7-chloro-3,4,5,6 tetra-hydro-α,α,4trimethylfuro[4,3,2-ef][3]benzazepine-2-methanol (2.3 mmol) in methylene.chloride (50 ml) stirred at 0° C. The mixture is stirred for 3 hours, diluted with water and basified with 10% aqueous sodium hydroxide. The organic phase is dried with magnesium sulfate and concentrated in vacuo to give an oil. The oil is dissolved in ethyl ether and treated with hydrogen chloride to give 7-chloro 3,4,5,6-tetrahydro-4-methyl-2-(1-methylethenyl)furo[4,3,2-ef][3]benzazepine hydrochloride.

EXAMPLE 35

(E)-7 Chloro 3,4,5,6-tetrahydro-4-methyl-2-[2-[(phenylmethoxy)methyl]ethenyl]furo[4,3,2-ef][3]benzazepine A mixture of 7-chloro-3,4,5,6-tetrahydro-4-methylfuro-[4,3,2-ef][3]benzazepine-2-carboxaldehyde, prepared as in Example 3, (0.2 g, 0.8 mmol), (2 hydroxyethyl)triphenylphosphonium chloride (0.34 g, 10 mmol) and potassium carbonate (1.4 g, 10 mmol) in benzyl alcohol (8 ml) was stirred at 100° C for 3 hours. The mixture was cooled, diluted with ethyl ether and filtered. The filtrate was washed with 3N hydrochloric (20 ml) and the aqueous phase was made alkaline and extracted with ethyl ether, dried with magnesium sulfate and concentrated in vacuo to qive an oil. The oil was dissolved in ethyl ether and treated with ethereal hydrogen chloride to give (E) 7-chloro-3,4,5,6-tetrahydro-4-methyl-2-[2[(phenylmethoxy)methyl]-ethenyl]-furo[4,3,2-ef][3]benzazepine hydrochloride.

EXAMPLE 36

(E)-1-(7-Chloro 3,4,5,6-tetrahydro 4-methylfuro[4,3,2-ef]-[3]benzazepin 2-yl)-1-hexen-3-one A mixture of 7-chloro 3,4,5,6 tetrahydro-4-methylfuro-4,3,2-ef][3]benzazepin-2 carboxaldehyde, prepared as in Example 3, ( 0.8 g, 3.2 mmol) dissolved in methylene chloride (4 ml), diethyl 1 (2 oxopentyl)phosphonate (0.75 g, 3.8 mmol) and potassium carbonate (0.88 g, 6.4 mmol) dissolved in water (1 ml) was stirred for 16 hours. The mixture was diluted with water and the organic phase was dried with sodium sulfate and concentrated in vacuo. The residue was recrystallized from ethyl acetate and ethyl ether to give 1-(7-chloro 3,4,5,6 tetrahydro-4-methylfuro-[4,3,2-ef][3]benzazepin 2-yl)-1-hexen-3-one; mp

118°–118.5° C.

EXAMPLE 37

(E)-1-(7-Chloro-3,4,5,6-tetrahydro-4-methylfuro[4,3,2-ef]-[3]benzazepin2-yl)1-hepten-3-one (E) 1-(7-Chloro-3,4,5,6-tetrahydro-4-methylfuro[4,3,2-ef]-[3]benzazepin-2-yl)-5-phenyl-1-penten-3-one Using the general procedure of Example 21, replacing 1-triphenylphosphoranylidene-2-propanone with 1-triphenylphosphoranylidene-2-hexanone or 4-phenyl-1-triphenylphosphoranylidene-2-butanone gave respectively:

(E)-1-(7chloro 3,4,5,6-tetrahydro-4-methylfuro[4,3,2-ef][3]-benzazepin 2-yl)-1-hepten-3-one hydrochloride: mp 235° C. (d) and (E)-1-(7-chloro-3,4,5,6-tetrahydro-4-methylfuro[4,3,2-ef]-[3]benzazepin-2-yl) 5phenyl-1-penten-3-one hydrochloride.

EXAMPLE 38

(E)-3-(7-Chloro-3,4,5,6-tetrahydro-4-methylfuro[4,3,2-ef]-[3]benzazepin- 2yl) N-ethyl-2-propenamide.

(E)-3 (7-Chloro-3,4,5,6-tetrahydro-4-methylfuro[4,3,2-ef]-[3]benzazepin-2-yl)-N,N-diethyl-2-propenamide, (E)-3-(7-Chloro-3,4,5,6-tetrahydro-4-methylfuro[4,3,2-ef]-[3]benzazepin-2-yl)-N-methyl-N-(phenylmethyl)-2-propenamide, (E)-3-(7-Chloro-3,4,5,6-tetrahydro-4-methylfuro[4,3,2-ef]-[3]benzazepin-2-yl)-N,N-bis(phenylmethyl)-2-propenamide Using the general procedure of Example 16, replacing ammonia with ethylamine, diethylamine, N-methylbenzylamine or N,N-dibenzylamine gave, respectively:

(E)-3-(7-chloro-3,4,5,6-tetrahydro-4-methylfuro[4,3,2-ef][3]benzazepin-2-yl)-N-ethyl-2-propenamide hydrochloride: mp 241°–242° C. (d), (E) -3-(7-chloro-3,4,5,6-1 -tetrahydro-4-methylfuro[4,3,2-ef]-[3]benzazepin-2-yl)-N,N-diethyl-2-propenamide hydrochloride: mp 233°–234° C. (d), (E)-3-(7-chloro-3,4,5,6-tetrahydro-4-methylfuro[4,3,2-ef]-[3]benzazepin-2-yl)-N-methyl-N-(phenylmethyl)-2-propenamide hydrochloride: mp 217°–219° C. (d), and (E)-3-(7-chloro-3,4,5,6-tetrahydro-4-methylfuro[4,3,2-ef]-[3]benzazepin-2-yl)-N,N-bis(phenylmethyl)-2-propenamide hydrochloride: mp °230–233° C. (d).

EXAMPLE 39

Phenylmethyl (E) 3-(7-Chloro-3,4,5,6-tetrahydro 4-methyl-furo[4,3,2-ef]([3]benzazepin-2-propenoate A solution of ethyl 3-(7-chloro-3,4,5,6-tetrahydro-4,5,6-tetrahydro-4-methylfuro[4,3,2-ef][3]benzazepin-2-yl)-2-propenoate, prepared as in Example 6, in benzyl alcohol (2 ml) was treated with a 60% dispersion of sodium hydride in mineral oil (14 mg) and stirred for 16 hours. The mixture was filtered and the filter cake dried to give phenylmethyl (E)-3-(7-chloro-3,4,5,6-tetrahydro-4-methylfuro[4,3,2 ef]-[3]benzazepin 2-yl) 2-propenoate: mp 240° C.

EXAMPLE 40

Propyl (E)-3-(7 Chloro-3,4,5,6 tetrahydro-4-methylfuro-[4,3,2-ef][3]benzazepin 2yl)-2-propenoate Propyl (E)-3-(7-Chloro 3,4,5,6-tetrahydro 4 methylfuro-[2-ef][3]benzazepin 2-yl)-2propenoate Using the general procedure of Example 39, replacing benzyl alcohol with propanol or 2-propanol gave, respectively:
propyl (E)-3-(7-chloro 3,4,5,6 tetrahydro 4-methyl-furo-[4,3,2-ef][3]benzazepin-2yl)-2-propenoate hydrochloride: mp 234°–235.5° C. (d) and
2-propyl (E) 3 (7 chloro-3,4,5,6 tetrahydro 4-methyl-furo-[4,3,2-ef][3]benzazepin 2-yl)-2-propenoate hydrochloride: mp 246.5°–248° C. (d).

EXAMPLE 41

(E)-7-Chloro 3,4,5,6 tetrahydro 4 methyl 2-[2 [(1,1-dimethylethyl)sulfonyl]ethenyl]furo[4,3,2,-ef][3]benzazepine (E)-7-Chloro-3,4,5,6-tetrahydro-4-methyl-2-[2-(phenylsulfonyl)ethenyl]furo[4,3,2-ef][3]benzazepine Using the general procedure of Example 22, replacing dimethyl [(methylsulfonyl)methyl]phosphonate with diethyl [[(1,1-dimethylethyl)sulfonyl]methyl]phosphonate or diethyl [(phenylsulfonyl)methyl]phosphonate gave respectively:
(E)-7 chloro 3,4,5,6 tetrahydro 4-methyl-2-[2 [(1,1-dimethylethyl)sulfonyl]ethenyl]furo[4,3,2-ef][3]benzazepine: mp 275° C. (d) and
(E) 7 chloro 3,4,5,6-tetrahydro-4-methyl-2 [2-(phenylsulfonyl)ethenyl]furo[4,3,2 ef][3]benzazepine hydrochloride: mp >235° C. (d).

EXAMPLE 42

(E)-2-(7-Chloro 3,4,5,6-tetrahydro-4-methylfuro[4,3,2-ef]-[3]benzazepin-2-yl)-N,N-diethyl-ethenesulfonamide A solution of N,N diethyl methanesulfonamide (4.7 g) in tetrahydrofuran (50 ml) was stirred at 20° C and treated with butyllithium in hexane (2.6 N, 27.9 ml) and diethyl chlorophosphate (5.2 ml). The cooling bath was removed and the mixture was stirred for 1.5 hours and poured onto ice. The resulting mixture was saturated with sodium bicarbonate, extracted with methylene chloride and the organic phase was washed with water, dried with sodium sulfate and magnesium sulfate, filtered and concentrated in vacuo to give diethyl [[(diethylamino)sulfonyl]methyl]-phosphonate.

A solution of diethyl [[(diethylamino)sulfonyl]methyl](0.44 g, 1.5 mmol) in 1.2-dimethoxyethane (1 phosphonat ml) was added to a suspension of sodium hydride (46 mg, 2 mmol) in 1,2 dimethoxyethane (4 ml) stirred at 0° C. The cooling bath was removed and the mixture was stirred at 25° C and treated with a solution of 7-chloro-3,4,5,6-tetra-hydro 4-methylfuro[4,3,2-ef][3]benzazepin-2-carboxaldehyde, prepared as in Example 3, (0.43 g, 1.7 mmol) in 1,2-dimethoxyethane (4 ml). The mixture was stirred for 16 hours, poured onto ice and extracted with methylene chloride. The organic phase was washed with water and dried with sodium sulfate and magnesium sulfate, filtered and concentrated in vacuo. The residue was chromatographed on silica qel eluted with methanol-ethyl acetate (3:97). Fractions containing the desired product were pooled, concentrated in vacuo, dissolved in methylene chloride-methanol, treated with ethereal hydroqen chloride and the resulting solid recrystallized from methanol to qive (E)-2-(7-chloro 3,4,5,6-tetrahydro 4-methylfuro-[4,3,2 ef][3]benzazepin-2-yl)-N,N-diethyl-ethenesulfonamide: mp 267° C. (d).

EXAMPLE 43

(E) 2-(7 Chloro 3,4,5,6-tetrahydro 4 methylfuro[4,3,2 ef]-3]benzazepin 2-yl) N,N-dipropyl-ethenesulfonamide, (E) 2-(7 Chloro 3,4,5,6-tetrahydro-4 methylfuro[4,3,2 ef]-[3]benzazepin 2-yl)-N methyl N-phenyl-ethenesulfonamide, (E) 2-(7-Chloro 3,4,5,6 tetrahydro 4-methylfuro[4,3,2-ef]-[3]benzazepin-2-yl) N-methyl-N-(phenylmethyl)-ethenesulfonamide, (E)-2-(7 Chloro-3,4,5,6-tetrahydro-4 methylfuro[4,3,2 ef]-[3]benzazepin-2-yl)-N,N bis(phenylmethyl)-ethenesulfonamide Using the general procedure of Example 42, replacing diethylamine with dipropylamine, N methylaniline, N-methylbenzylamine or N,N dibenzylamine gave:
(E)-2-(7-chloro 3,4,5,6-tetrahydro 4-methyl-furo[4,3,2-ef]-[3]benzazepin-2-yl)-N,N-dipropyl-ethenesulfonamide: mp 243° C. (d),
(E)-2-(7 chloro 3,4,5,6 tetrahydro 4-methylfuro[4,3,2-ef]-[3]benzazepin-2-yl) N-methyl-N-phenyl-ethenesulfonamide: mp 251°–252° C. (d),
(E) 2-(7-chloro-3,4,5,6 tetrahydro 4 methylfuro[4,3,2 ef]-[3]benzazepin-2yl)-N methyl-N-(phenylmethyl)-ethenesulfonamide: mp 232°–232.5° C. (d), and
(E) 2-(7-chloro 3,4,5,6 tetrahydro 4 methylfuro[4,3,2 ef][3]benzazepin 2-yl) N,N-bis(phenylmethyl)-ethenesulfonamide: mp 229°–230.5° C. (d).

EXAMPLE 44

An oral dosage form for administerinq the presently invented compounds is produced by screeninq mixing and filling into a hard gelatin capsule ingredients in the proportions shown in Table II, below.

TABLE II

| Ingredients | Amounts |
| --- | --- |
| Ethyl (E)-3-(7-Chloro-3,4,5,6-tetrahydro-4-methylfuro[4,3,2-ef][3]benzazepin-2-yl)-2-propenoate | 50 mg |
| magnesium stearate | 5 mg |
| lactose | 75 mg |

EXAMPLE 45

The sucrose, calcium sulfate dihydrate and Formula (I) compound shown in Table III below, are mixed and granulated with a 10% gelatin solution. The wet granules are screened, dried, mixed with the starch, talc and stearic acid, screened and compressed into a tablet.

TABLE III

| Ingredients | Amounts |
| --- | --- |
| 7-Chloro-3,4,5,6-tetrahydro-4-methyl-2-(2-methyl-2-propenyl)-furo[4,3,2-ef][3]benzazepine | 100 mg |
| calcium sulfate dihydrate | 150 mg |
| sucrose | 20 mg |
| starch | 10 mg |
| talc | 5 mg |
| stearic acid | 3 mg |

EXAMPLE 46

7-Chloro-2-ethenyl-3,4,5,6-tetrahydro-4-methyl-furo[4,3,2-ef][3]benzazepine hydrochloride, 75 mg, is dispersed in 25 ml of normal saline to prepare an injectable preparation.

Contemplated equivalents of Formula (I) compounds are compounds that upon administration to mammals, including humans, are metabolized to Formula (I) compounds or metabolized to any Formula (I) compound active metabolites at a sufficient rate and in sufficient amounts to produce physiologic activity of Formula (I) compounds. Such compounds also would be included in the invented pharmaceutical compositions and used in the invented methods.

While the preferred embodiments of the invention are illustrated by the above, the invention is not limited to the precise instructions herein disclosed and that the right to all modifications coming within the scope of the following claims is reserved.

What is claimed is:

1. A compound represented by the formula:

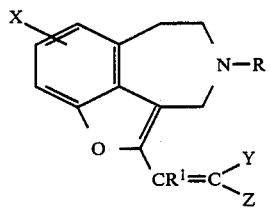

in which: X is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, $SC_{1-4}$alkyl, $S(CH_2)_{0-6}$aryl, $SCF_3$, or any accessible combination thereof of up to three substituents;

R is H, $C_{1-6}$alkyl or $C_{3-5}$alkenyl;

$R^1$ is H or $C_{1-6}$alkyl;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl;

$R^{12}$ is H, $C_{1-6}$alkyl, $COR^{14}$, or $SO_2R^{15}$;

$R^{13}$ is H or $C_{1-6}$alkyl;

$R^{14}$ and $R^{15}$ independently are $C_{1-6}$alkyl or $(CH_2)_{0-6}$aryl;

Y and Z independently are H, $NO_2$, $C_{1-6}$alkyl, $CH_2CH_2OH$, CN, $CH_2OR^2$, $CH_2SR^2$, $COR^2$, $CO_2R^2$, $CONR^3R^4$, $SO_2NR^3R^4$, $SO_3R^2$, $SO_2R^5$, $SOR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, halo, $CF_3$, or $(CH_2)_{0-6}$aryl;

$R^2$, $R^3$, and $R^4$ independently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$ alkenyl, or $(CH_2)_{0-6}$aryl; or a pharmaceutically acceptable salt thereof.

2. A compound of claim 1 having the formula:

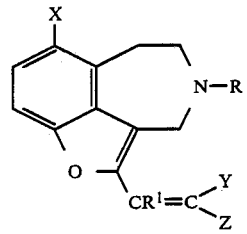

in which:

X is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, $SCl_4$alkyl, $S(CH_2)_{0-6}$ar $SC_{1-4}$alkyl, $S(CH_2)_{0-6}$aryl, or $SCF_3$;

R is H, $C_{1-6}$alkyl, or $C_{3-5}$alkenyl;

$R^1$ is H or $C_{1-6}$alkyl;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl;

$R^{12}$ is H, $C_{1-6}$alkyl, $COR^{14}$, or $SO_2R^{15}$;

$R^{13}$ is H or $C_{1-6}$alkyl;

$R^{14}$ and $R^{15}$ independently are $C_{1-6}$alkyl or $(CH_2)_{0-6}$aryl;

Y and Z independently are H, $NO_2$, $C_{1-6}$alkyl, $CH_2CH_2OH$, CN, $CH_2OR^2$, $CH_2SR^2$, $COR^2$, $CO_2R^2$, $CONR^3R^4$, $SO_2NR^3R^4$, $SO_3R^2$, $SO_2R^5$, $SOR^5$, $P(O)(OR^3)(OR^4)$, $P(O)R^5(OR^3)$, $P(O)R^5R^6$, $P(O)(OR^2NR^3R^4$, $P(O)(NR^3R^4)_2$, $P(O)R^5(NR^3R^4)$, halo, $CF_3$, or $(CH_2)_{0-6}$aryl;

$R^2$, $R^3$, and $R^4$ independently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$alkenyl, or $(CH_2)_{0-6}$aryl; or a pharmaceutically acceptable salt thereof.

3. A compound of claim 2 wherein X is Cl, Br, F, or I.

4. A compound of claim 3 wherein R is H, $CH_3$, $CH_2CH_3$, or $CH_2CH=CH_2$.

5. A compound of claim 4 that is 7-chloro-2-ethenyl-3,4,5,6-tetrahydro-4-methylfuro[4,3,2-ef][3]benzazepine, or a pharmaceutically acceptable salt thereof.

6. A compound of claim 4 that is:

(E)-3-(7-chloro-3,4,5,6-tetrahydro-4-methylfuro-[4,3,2-ef][3]benzazepin-2-yl)-2-propenoic acid;

ethyl (E)-3-(7-chloro-3,4,5,6-tetrahydro-4-methylfuro[4,3,2-ef][3]benzazepin-2-yl)-2-propenoate;

ethyl (E)-3-(7-chloro-3,4,5,6-tetrahydro-4-methylfuro[4,3,2-ef][3]benzazepin-2-yl)-2-methyl-2-propenoate;

7-chloro-3,4,5,6-tetrahydro-4-methyl-2-(2-methyl-1-propenyl)furo[4,3,2-ef][3]benzazepine;

ethyl (E)-3(7-chloro-3,4,5,6-1 -tetrahydrofuro-[4,3,2-ef][3]benzazepin-2-yl)-2-propenoate;

ethyl (E)-3[7-chloro-3,4,5,6-tetrahydro-4-(2propenyl)furo[4,3,2-ef][3]benzazepin-2-yl]-2-propenoate;

ethyl (E)-3-(7-chloro-3,4,5,6-tetrahydro-4-methylfuro[4,3,2-ef][3benzazepin-2-yl)-2-propyl-2-propenoate; chloride ethyl (Z)-3-(7-chloro-3,4,5,6-tetrahydro-4-methylfuro[4,3,2-ef][3]benzazepn-2-yl)-2-fluoro-2-propenoate;

ethyl (E)-2-chloro-3-(7-chloro-3,4,5,6-tetrahydro-4-methylfuro[4,3,2-ef][3]benzazepin-2-yl)-2-propenoate;

ethyl (Z)-2-chloro-3(7-chloro-3,4,5,6-tetrahydro-4-methylfuro[4,3,2-ef][3]benzazepin-2-yl)-2-propenoate;

ethyl (Z)-2-bromo-3-(7-chloro-3,4,5,6-tetrahydro-4-methylfuro[4,3,2-ef][3]benzazepin-2-yl)-2-propenoate;

methyl (E)-3-(7-chloro-3,4,5,6-tetrahydro-4-methylfuro[4,3,2-ef][3benzazepin-2-yl)-2-propenoate;

(E)-3-(7-chloro-3,4,5,6-tetrahydro-4-methylfuro[4,3,2-ef][3]benzazepin-2-yl)-2-propenamide;

(E)-3-(7-chloro-3,4,5,6-tetrahydro-4-methylfuro[4,3,2-ef][3]benzazepin-2-yl)-N-methyl-2-propenamide;

(E)-3-(7-chloro-3,4,5,6-tetrahydro-4-methylfuro[4,3,2-ef][3]benzazepin-2yl)-N,N-dimethyl-2-propenamide;

(E)-3-(7-chloro-3,4,5,6-tetrahydro-4-methylfuro[4,3,2-ef][3]benzazepin-2-yl)-N,2-dimethyl-2-propenamide;

(E)-3-(7-chloro-3,4,5,6-tetrahydro-4-methylfuro[4,3,2-ef][3]benzazepin-2-yl)-2-propenenitrile;

(E)-4-(7-chloro-3,4,5,6-tetrahydro-4-methylfuro[4,3,2-ef][3]benzazepin-2-yl)-3-buten-2-one;

(E)-7-chloro-3,4,5,6-tetrahydro-4-methyl-2-[2-(methylsulfonyl)ethenyl]furo[4,3,2-ef][3]benzazepine;

(E)-2-(7-chloro-3,4,5,6-tetrahydro-4-methylfuro[4,3,2-ef][3]benzazepin-2yl)-N,N-dimethylethenesulfonamide;

diethyl (E)-[2-(7-chloro-3,4,5,6-tetrahydro-4-methylfuro[4,3,2-ef][3]benzazepin-2-yl)-ethenyl]phosphonate;

methyl (Z)-3-(7-chloro-3,4,5,6-tetrahydro-4-methylfuro[4,3,2-ef][3]benzazepin-2-yl)-2-propenoate;

ethyl (E)-3(7-chloro-4-ethyl-3,4,5,6-tetrahydrofuro[4,3,2-ef][3]benzazepin-2-yl)-2-propenoate;

(E)-3-(7-chloro-3,4,5,6-tetrahydro-4-methylfuro[4,3,2-ef][3]benzazepin-2-yl)-2-propen-1-ol;

7-chloro-3,4,5,6-tetrahydro-4-methyl-2-[2-[(phenylmethoxy)methyl]ethenyl]furo[4,3,2-ef][3]benzazepine;

(E)-1-(7-chloro-3,4,5,6-tetrahydro-4-methylfuro[4,3,2-ef][3]benzazepin-2-yl)-1-hexen-3-one;

(E)-1-(7-chloro-3,4,5,6-tetrahydro-4-methylfuro[4,3,2-ef][3]benzazepin-2yl)-1-hepten-3-one;

(E)-1-(7-chloro-3,4,5,6-tetrahydro-4-methylfuro[4,3,2-ef][3]benzazepin-2yl)-5-phenyl-1-penten-3-one;

(E) 3-(7 chloro 3,4,5,6-tetrahydro-4-methylfuro[4,3,2-ef][3]benzazepin-2-yl)-N-methyl-2(2-hydroxyethyl)-2-propenamide;

(E) 3 (7-chloro 3,4,5,6 tetrahydro 4 methylfuro[-4,3,2-ef][3]benzazepin-2-yl) N ethyl 2-propenamide;

(E)-3-(7 chloro 3,4,5,6 tetrahydro 4 methylfuro[-4,3,2-ef][3]benzazepin-2yl)-N,N-diethyl-2-propenamide;

(E)-3 (7 chloro 3,4,5,6 tetrahydro 4-methylfuro-[-4,3,2 ef][3]benzazepin-2-yl)-N-methyl-N-(phenylmethyl)-2-propenamide;

(E)-3 (7 chloro 3,4,5,6 tetrahydro 4-methylfuro[-4,3,2-ef][3]benzazepin 2-yl)-N,N bis(phenylmethyl)-2-propenamide;

propyl (E) 3-(7 chloro-3,4,5,6-tetrahydro 4-methylfuro[4,3,2-ef][3]benzazepin-2-yl)-2-propenoate;

2-propyl (E)-3-(7-chloro-4,5,6-tetrahydro- 4-methylfuro[4,3,2-ef][3]benzazepin-2-yl)-2-propenoate;

phenylmethyl (E) 3 (7 chloro-3,4,5,6 tetrahydro 4-methylfuro[4,3,2-ef][3]benzazepin-2-yl)-2-propenoate;

ethyl (E)-3 (7 chloro 3,4,5,6 tetrahydro 4-methylfuro[4,3,2-ef][3]benzazepin 2 yl)-2-phenyl-2-propenoate;

ethyl (Z) 3-(7 chloro 3,4,5,6 tetrahydro-4-methylfuro[4,3,2-ef][3]benzazepin-2-yl)-2-phenyl-2-propenoate;

(E)-7-chloro 3,4,5,6 tetrahydro 4 methyl 2 [2-[1,1-dimethylethyl)sulfonyl]ethenyl]furo[4,3,2-ef][3]-benzazepine;

(E)-2-(7 chloro 3,4,5,6-tetrahydro-4-methyl-2-[2-phenylsulfonyl)ethenyl]furo[4,3,2-ef][3]benzazepine;

(E) 2-(7-chloro 3,4,5,6-tetrahydro-4 methylfuro-[4,3,2-ef][3]benzazepin-2-yl)-N,N-diethyl-ethenesulfonamide;

(E) 2-(7-chloro-3,4,5,6-tetrahydro-4-methylfuro-[4,3,2-ef][3]benazaepin-2-yl)-N,N-dipropyl-ethenesulfonamide;

(E) 2 (7 chloro-3,4,5,6-tetrahydro 4-methylfuro-[4,3,2-ef][3]benzazepin 2-yl)-N-methyl-N-phenyl-ethenesulfonamide;

(E) 2-(7-chloro 3,4,5,6-tstrahydro 4 methylfuro-[4,3,2-ef][3]benzazepin-2-yl)-N-methyl-N-phenylmethyl)-ethenesulfonamide; or (E)-2 (7 chloro-3,4,5,6-tetrahydro 4 methylfuro-[4,3,2-ef][3]benzazepin 2yl) N,N-bis(phenylmethyl)-ethene-sulfonamide;

or a pharmaceutically acceptable salt thereof.

7. A pharmaceutical composition comprising a compound of claim 1 and a suitable pharmaceutical carrier.

8. A pharmaceutical composition of claim 7 wherein the compound is 7-chloro-2 ethenyl-3,4,5,6-tetrahydro 4-methylfuro[4,3,2 ef][3]benzazepine, or a pharmaceutically acceptable salt thereof.

9. A pharmaceutical composition of claim 7 wherein the compound is:

(E) 3 (7 chloro-3,4,5,6 tetrahydro 4-methylfuro-[4,3,2-ef][3]benzazepin-2-yl)-2 propenoic acid;

ethyl (E) 3-(7 chloro-3,4,5,6-tetrahydro 4-methylfuro-4,3,2-ef][3]benzazepin-2-yl)-2-propenoate;

ethyl (E)-3-(7-chloro 3,4,5,6 tetrahydro-methylfuro[4,3,2-ef][3]benzazepin-2-yl) 2-methyl-2-propenoate;

7-chloro 3,4,5,6 tetrahydro 4 methyl-2 (2-methyl-1-propenyl)furo[4,3,2-ef][3]benzazepin;

ethyl (E) 3-(7 chloro 3,4,5,6 tetrahydrofuro-[4,3,2-ef][3]benzazepin-2-yl)-2-propenoate;

ethyl (E) 3-[7 chloro 3,4,5,6 tetrahydro 4-(2-propenyl)furo[4,3,2-ef][3]benzazepin 2-yl]-2-propenoate;

ethyl (E)-3 (7-chloro-3,4,5,6 tetrahydro 4-methylfuro[4,3,2-ef][3]benzazepin 2 yl) 2-yl)-2-propyl-2-propenoate;

ethyl (Z)-3 (7-chloro 3,4,5,6 tetrahydro-4-methylfuro[4,3,2-ef][3]benzazepin-2-yl)-2-fluoro-2-propenoate;

ethyl (E)-2-chloro-3-(7-chloro-3,4,5,6-tetrahydro-4-methylfuro[4,3,2-ef][3]benzazepin-2-yl)-2-propenoate;

ethyl (Z)-2-chloro-3-(7-chloro-3,4,5,6-tetrahydro-4-methylfuro[4,3,2-ef][3]benzazepin-2-yl)-2-propenoate;

ethyl (Z)-2-bromo-3-(7-chloro-3,4,5,6-tetrahydro-4-methylfuro[4,3,2-ef][3]benzazepin-2-yl)-2-propenoate;

methyl (E) 3 (7-chloro-3,4,5,6-tetrahydro-4-methylfuro[4,3,2-ef][3]benzazepin 2-yl)-2 propenoate;

(E)-3 (7 chloro 3,4,5,6 tetrahydro 4-methylfuro[4,3,2-ef][3]benzazepin-2-yl) 2-propenamide;

(E) 3-(7-chloro 3,4,5,6 tetrahydro 4-methylfuro[4,3,2 ef][3]benzazepin-2-yl) N-methyl-2-propenamide;

(E) 3 (7-chloro 3,4,5,6 tetrahydro-4-methylfuro[4,3,2 ef][3]benzazepin-2yl) N,N-dimethyl-2-propenamide;

(E)-3 (7 chloro-3,4,5,6 tetrahydro 4-methylfuro[-4,3,2-ef][3]benzazepin-2-yl) N,2-dimethyl-2-propenamide;

(E) 3 (7 chloro 3,4,5,6-tetrahydro 4-methylfuro[-4,3,2-ef][3]benzazepin-2yl)-2-propenenitrile;

(E) 4 (7 chloro-3,4,5,6 tetrahydro-4-methylfuro[4,3,2-ef][3]benzazepin-2-yl)-3buten-2-one;

(E) 7-chloro 3,4,5,6-tetrahydro-4 methyl-2 [2-(methylsulfonyl)ethenyl]furo[4,3,2-ef][3]benzazepine;

(E)-2 (7-chloro 3,4,5,6 tetrahydro-4-methylfuro[-4,3,2 ef][3]benzazepin-2-yl)-N,N-dimethylethenesulfonamide;

diethyl (E)-[2 (7 chloro 3,4,5,6 tetrahydro-4-methylfuro[4,3,2 ef][3]benzazepin-2yl)ethenyl]phosphonate;

methyl (Z)-3-(7-chloro-3,4,5,6-tetrahydro-4-methylfuro[4,3,2-ef][3]benzazepin-2 yl)-2-propenoate;

ethyl (E)-3 (7-chloro-4 ethyl-3,4,5,6-tetrahydrofuro[4,3,2 ef][3]benzazepin 2 yl)-2-propenoate;

(E)-3-(7 chloro 3,4,5,6 tetrahydro-4 methylfuro[4,3,2-ef][3]benzazepin 2 yl)-2-propen-1-ol;

chloro-3,4,5,6 tetrahydro 4 methyl 2-[2 [(phenylmethoxy)methyl]ethenyl]furo[4,3,2-ef][3]benzazepine;

(E)-1-(7-chloro-3,4,5,6-tetrahydro-4-methylfuro[4,3,2-ef][3]benzazepin-2-yl)-1-hexen-3-one;

(E)-1-(7chloro-3,4,5,6 tetrahydro-4-methylfuro[4,3,2-ef][3]benzazepin-2-yl) 1-hepten-3-one;

(E) 1-(7-chloro 3,4,5,6-tetrahydro- 4-methylfuro[4,3,2-ef][3]benzazepin-2yl)-5-phenyl-1-penten-3-one;

(E)-3-(7-chloro-3,4,5,6-tetrahydro-4-methylfuro[4,3,2-ef][3]benzazepin-2-yl)-N-methyl-2-(2-hydroxyethyl)-2-propenamide;

(E)-3 (7 chloro 3,4,5,6 tetrahydro-4-methylfuro[4,3,2-ef][3]benzazepin-2-yl)-N-ethyl-2-propenamide;

(E) 3 (7-chloro 3,4,5,6 tetrahydro 4-methylfuro[4,3,2-ef][3]benzazepin 2-yl)-N,N-diethyl-2-propenamide;

(E)-3 (7 chloro 3,4,5,6 tetrahydro 4 methylfuro-[4,3,2 ef][3]benzazepin-2-yl) N methyl-N-(phenylmethyl)-2-propenamide;

(E)-3-(7-chloro-3,4,5,6 tetrahydro 4 methylfuro[4,3,2-ef][3]benzazepin 2yl)-N,N-bis(phenylmethyl)-2-propenamide;

propyl (E) 3 (7 chloro 3,4,5,6 tetrahydro 4-methylfuro[4,3,2 ef][3]benzazepin-2-yl) 2-propenoate;

2-propyl (E) 3 (7 chloro 3;4,5,6-tetrahydro 4-methylfuro[4,3,2-ef][3]benzazepin 2-yl)-2-propenoate;

phenylmethyl (E) 3-(7 chloro-3,4,5,6 tetrahydro 4-methylfuro[4,3,2 ef][3]benzazepin 2-yl)-2-propenoate;

ethyl (E)-3 (7 chloro 3,4,5,6 tetrahydro 4-methylfuro[4,3,2 ef][3]benzazepin 2-yl) 2-phenyl-2-propenoate;

ethyl (Z) 3-(7-chloro 3,4,5,6-tetrahydro 4methylfuro[4,3,2-ef][3]benzazepin 2-yl)-2-phenyl-2-propenoate;

(E) 7 chloro 3,4,5,6 tetrahydro 4 methyl-2 [2-[1,1-dimethylethyl)sulfonyl]ethenyl]furo[4,3,2-ef][3]benzazepine;

(E)-7-chloro-3,4,5,6-tetrahydro- 4 methyl-2-phenylsulfonyl)ethenyl]furo[4,3,2-ef][3]benzazepine;

(E)-2-(7-chloro-3,4,5,6-tetrahydro-4 methylfuro[4,3,2-ef][3]benzazepin-2-yl)-N,N-diethylethenesulfonamide;

(E)-2-(7-chloro-3,4,5,6 tetrahydro 4-methylfuro[4,3,2 ef][3]benzazepin-2-yl) N,N-dipropylethenesulfonamide;

(E)-2-(7 chloro-3,4,5,6 tetrahydro 4 methylfuro-[4,3,2 ef][3]benzazepin-2-yl)-N-methyl-N-phenylethenesulfonamide;

(E)-2-(7-chloro-3,4,5,6 tetrahydro-4-methylfuro[4,3,2 ef][3]benzazepin-2-yl)-N-methyl-N-phenylmethyl)-ethenesulfonamide; or (E)-2 (7 chloro 3,4,5,6-tetrahydro 4-methylfuro[4,3,2-ef][3]benzazepin-2-yl) N,N bis(phenylmethyl)-ethene-sulfonamide.

10. A method of antagonizing α-adrenergic receptors in mammals that comprises administering to a subject in need thereof an effective amount of a compound of claim 1.

11. A method of claim 10 wherein the compound is 7-chloro 2 ethenyl 3,4,5,6 tetrahydro 4-methylfuro[4,3,2-ef][3]benzazepine.

12. A method of claim 10 wherein the compound is:
(E) 3-(7 chloro 3,4,5,6 tetrahydro 4-methylfuro[4,3,2-ef][3]benzazepin-2-yl)-2-propenoic acid;

ethyl (E) 3 (7 chloro-3,4,5,6 tetrahydro-4-methylfuro[4,3,2 ef][3]benzazepin-2yl) 2-propenoate;

ethyl (E) 3(7 chloro 3,4,5,6 tetrahydro-4 methyl-furo[4,3,2-ef][3]benzazepin-2-yl) 2-methyl-2-propenoate;

7-chloro-3,4,5,6-tetrahydro-4-methyl-2-(2-methyl-1-propenyl)furo[4,3,2-ef][3]benzazepine;

ethyl (E)-3-(7-chloro-3,4,5,6-tetrahydrofuro-[4,3,2-ef][3]benzazepin-2-yl)-2-propenoate;

ethyl (E) 3 [7 chloro 3,4,5,6 tetrahydro-4-(2-propenyl)furo[4,3,2-ef][3]benzazepin-2-yl]-2-propenoate;

ethyl (E)-3 (7 chloro 3,4,5,6-tetrahydro-4-methylfuro[4,3,2 ef][3]benzazepin-2yl)-2-propyl-2-propenoate;

ethyl (Z)-3-(7-chloro-3,4,5,6-tetrahydro-4-methyl furo[4,3,2-ef][3]benzazepin-2-yl)-2-fluoro-2-propenoate;

ethyl (E)-2-chloro-3-(7-chloro-3,4,5,6-tetrahydro-4-methylfuro[4,3,2-ef][3]benzazepin-2-yl)-2-propenoate;

ethyl (Z)-2-chloro-3-(7-chloro-3,4,5,6-tetrahydro-4-methylfuro[4,3,2-ef][3benzazepin-2-yl)-2-propenoate;

ethyl (Z)-2-bromo3-(7-chloro-3,4,5,6-tetrahydro-4-methylfuro[4,3,2-ef][3]benzazepin-2-yl)-2-propenoate;

methyl (E)-3-(7-chloro-3,4,5,6-tetrahydro-4-methylfuro[4,3,2-ef][3]benzazepin-2-yl-2-propenoate;

(E)-3-(7-chloro-3,4,5,6 tetrahydro-4methylfuro-[4,3,2 ef][3]benzazepin-2-yl)-2-propenamide;
(E)-3-(7-chloro-3,4,5,6-tetrahydro-4-methyl-furo[4,3,2-ef][3]benzazepin-2yl)-N-methyl-2-propenamide;
(E)-3-(7-chloro-3,4,5,6-tetrahydro-4-methyl-furo[4,3,2-ef][3]benzazepin-2-yl)-N,N-dimethyl-2-propenamide;
(E)-3-(7-chloro-3,4,5,6-tetrahydro-4-methyl-furo[4,3,2-ef][3]benzazepin-2-yl)-N,2-dimethyl-2-propenamide;
(E)-3-(7-chloro-3,4,5,6-tetrahydro-4-methyl-furo[4,3,2-ef][3]benzazepin-2-yl)-2-propenenitrile;
(E)-4-(7-chloro-3,4,5,6-tetrahydro 4-methylfuro[-4,3,2 ef][3]benzazepin-2yl)-3-buten-2-one;
(E) 7 chloro 3,4,5,6-tetrahydro 4-methyl-2-[2(methylsulfonyl)ethenyl]furo[4,3,2-ef][3]benzazepine;
(E) 2 (7 chloro-3,4,5,6 tetrahydro-4methylfuro[4,3,2-ef][3]benzazepin-2-yl) N,N-dimethylethenesulfonamide;
diethyl (E) [2-(7-chloro-3,4,5,6-tetrahydro 4-methyl-furo[4,3,2-ef][3]benzazepin2-yl)ethenyl]phosphonate;
methyl (Z)-3-(7 chloro 3,4,5,6 (tetrahydro-4-methyl-furo[4,3,2 ef][3]benzazepin-2-yl) 2-propenoate;
ethyl (E)-3 (7-chloro-4 ethyl-3,4,5,6-tetrahydrofuro[4,3,2 ef][3]benzazepin-2-yl)-2-propenoate.
(E) 3 (7 chloro 3,4,5,6 tetrahydro 4 methylfuro-[4,3,2 ef][3]benzazepin-2-yl) 2propen-1-ol;
7 chloro 3,4,5,6-tetrahydro-4-methyl-2-[2-[(phenylmethoxy)methyl]ethenyl]furo[4,3,2-ef][3]benzazepine;
(E) 1-(7-chloro 3,4,5,6 tetrahydro-4-methylfuro-[4,3,2-ef][3]benzazepin-2-yl) 1-hexen-3-one;
(E) 1 (7 chloro 3,4,5,6 tetrahydro 4-methylfuro-[4,3,2-ef][3]benzazepin-2-yl) 1hepten-3-one;
(E) 1 (7-chloro 3,4,5,6 tetrahydro-4-methylfuro-[4,3,2-ef][3]benzazepin-2-yl)-5-phenten-3-one;
(E) 3-(7 chloro 3,4,5,6-tetrahydro-4-methylfuro-[4,3,2-ef][3]benzazepin-2-yl)-N-methyl-2-(2-hydroxyethyl)-2-propenamide;
(E)-3-(7-chloro 3,4,5,6-tetrahydro 4 methylfuro-[4,3,2 ef][3]benzazepin-2yl)-N ethyl-2-propenamide;
(E)-3-(7-chloro 3,4,5,6-tetrahydro 4-methyl-furo-[4,3,2-ef][3]benzazepin-2yl)-N,N-diethyl-2-propenamide;
(E) 3 (7 chloro 3,4,5,6 tetrahydro-4-methylfuro-[4,3,2-ef][3]benzazepin-2-yl)-N-methyl-N-(phenylmethyl)-2-propenamide;
(E)-3-(7-chloro-3,4,5,6 tetrahydro 4-methylfuro-[4,3,2 ef][3]benzazepin-2yl)-N,N-bis(phenylmethyl)-2-propenamide;
propyl (E)-3 (7-chloro-3,4,5,6-tetrahydro-4methyl-furo-[4,3,2 ef][3]benzazepin-2yl) 2-propenoate;
2-propyl (E) 3 (7 chloro-3,4,5,6-tetrahydro-4-methyl-furo[4,3,2 ef][3]benzazepin-2-yl)-2-propenoate;
phenylmethyl (E) 3 (7 chloro 3,4,5,6-tetrahydro 4-methylfuro[4,3,2-ef][3]benzazepin-2-yl)-2-propenoate;
ethyl (E)-3-(7-chloro-3,4,5,6-tetrahydro-4-methyl-furo[4,3,2 ef][3]benzazepin-2-yl)-2-phenyl-2-propenoate;
ethyl (Z) 3 (7 chloro 3,4,5,6 tetrahydro 4-methyl-furo[4,3,2-ef][3]benzazepin 2yl) 2-phenyl-2-propenoate;
(E) 7-chloro 3,4,5,6 tetrahydro 4 methyl 2 [2-[1,1 dimethylethyl)sulfonyl]ethenyl]furo[4,3,2-ef][3]-benzazepine;
(E) 7-chloro 3,4,5,6 tetrahydro 4 methyl-2 [2-phenylsulfonyl)ethenyl]furo[4,3,2-ef][3]benzazepine;
(E) 2 (7 chloro 3,4,5,6 tetrahydro 4 methylfuro-[4,3,2 ef][3]benzazepin-2-yl)-N,N-diethyl-ethenesulfonamide;
(E) 2 (7 chloro 3,4,5,6 tetrahydro 4 methylfuro-[4,3,2 ef][3]benzazepin 2yl)-N,N-dipropyl-ethenesulfonamide;
(E) 2 (7 chloro 3,4,5,6 tetrahydro 4 methylfuro-[4,3,2-ef][3]benzazepin 2yl)-N-methyl-N-phenyl-ethenesulfonamide;
(E) 2-(7 chloro 3,4,5,6 tetrahydro 4 methylfuro-[4,3,2 ef][3]benzazepin 2yl)-N-methyl-N-phenylmethyl)-ethenesulfonamide; or
(E) 2 (7 chloro 3,4,5,6 tetrahydro 4 methylfuro-[4,3,2 ef][3]benzazepin-2-yl)-N,N-bis(phenylmethyl)-ethenesulfonamide.

13. A method of reducing blood pressure in mammals that comprises administering to a subject in need thereof an effective amount of a compound of claim 1.

14. A method of treating cardiovascular diseases in mammals that comprises administering to a subject in need thereof an effective amount of a compound of claim 1.

15. A method of treating benign prostatic hypertrophy in mammals that comprises administering to a subject in need thereof an effective amount of a compound of claim 1.

16. A method of treating benign prostatic hypertrophy in mammals that comprises administering to a subject in need thereof an effective amount of a compound of claim 1.

* * * * *

UNITED STATES PATENT AND TRADEMARK OFFICE
CERTIFICATE OF CORRECTION

Page 1 of 2

PATENT NO. : 4,959,360

DATED : September 25, 1990

INVENTOR(S) : Lafferty, et al.

It is certified that error appears in the above-identified patent and that said Letters Patent is hereby corrected as shown below:

In Claim 1, at column 29, line 53, replace "$(CH_2)_{0-6-1}$ aryl" with -- $(CH_2)_{0-6}$aryl ---.

In Claim 1, at column 29, line 66, replace "$CH_2ORhu\ 2$" with -- $CH_2OR^2$ --.

In Claim 2, at column 30, line 22, after "$OR^{12}$," delete "SCl".

In Claim 2, at column 30, line 23, delete "4alkyl,S(CH2)O 6ar".

In Claim 2, at column 30, line 39 replace "$P(O)(OR^2NR^3R^4$" with -- $P(O)(OR^2)NR^3R^4$ --.

In Claim 6, at column 31, line 3, after "propenoate;" delete "chloride".

In Claim 14, column 36, lines 40-43, delete entire claim.

In Claim 15, at column 36, lines 44-48, delete entire claim.

UNITED STATES PATENT AND TRADEMARK OFFICE
CERTIFICATE OF CORRECTION

PATENT NO. : 4,959,360

DATED : September 25, 1990

INVENTOR(S) : Lafferty, et al.

It is certified that error appears in the above-identified patent and that said Letters Patent is hereby corrected as shown below:

Column 36, lines 40-48 claims 14 & 15 should be changed to read as shown below

14. A method of treating peripheral vascular disease in mammals that comprises administering to a subject in need thereof an effective amount of a compound of claim 1.

15. A method of treating congestive heart failure in mammals that comprises administering to a subject in need thereof an effective amount of a compound of claim 1.

Signed and Sealed this

Thirty-first Day of December, 1991

*Attest:*

HARRY F. MANBECK, JR.

*Attesting Officer*  *Commissioner of Patents and Trademarks*